US007772225B2

(12) United States Patent
Antel et al.

(10) Patent No.: US 7,772,225 B2
(45) Date of Patent: Aug. 10, 2010

(54) N-SULFAMOYL-PIPERIDINEAMIDES FOR THE TREATMENT OR INHIBITION OF OBESITY AND RELATED CONDITIONS

(75) Inventors: Jochen Antel, Bad Muender (DE); Michael Firnges, Barsinghausen (DE); Uwe Schoen, Burgdorf (DE); Harald Waldeck, Isernhagen (DE); Michael Wurl, Garbsen (DE); Dania Reiche, Adelheidsdorf (DE); Peter-Colin Gregory, Hannover (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 225 days.

(21) Appl. No.: 11/635,514

(22) Filed: Dec. 8, 2006

(65) Prior Publication Data

US 2007/0149512 A1 Jun. 28, 2007

Related U.S. Application Data

(60) Provisional application No. 60/749,127, filed on Dec. 9, 2005.

(51) Int. Cl.

| | |
|---|---|
| ***A01N 43/00*** | (2006.01) |
| ***A01N 43/58*** | (2006.01) |
| ***A01N 43/40*** | (2006.01) |
| ***A61K 31/55*** | (2006.01) |
| ***A61K 31/54*** | (2006.01) |
| ***A61K 31/535*** | (2006.01) |
| ***A61K 31/50*** | (2006.01) |
| ***A61K 31/497*** | (2006.01) |
| ***A61K 31/445*** | (2006.01) |
| ***C07D 223/14*** | (2006.01) |
| ***C07D 279/12*** | (2006.01) |
| ***C07D 295/00*** | (2006.01) |
| ***C07D 265/28*** | (2006.01) |
| ***C07D 239/00*** | (2006.01) |
| ***C07D 239/70*** | (2006.01) |
| ***C07D 471/00*** | (2006.01) |
| ***C07D 487/00*** | (2006.01) |
| ***C07D 241/04*** | (2006.01) |
| ***C07D 211/00*** | (2006.01) |

(52) U.S. Cl. .............................. 514/213.01; 514/224.5; 514/231.2; 514/247; 514/252.12; 514/315; 540/576; 544/59; 544/98; 544/245; 544/258; 546/184

(58) Field of Classification Search ....................... None
See application file for complete search history.

(56) References Cited

U.S. PATENT DOCUMENTS

| | | | |
|---|---|---|---|
| 2003/0171360 | A1 | 9/2003 | Gross et al. |
| 2004/0006086 | A1 | 1/2004 | Stamford et al. |

FOREIGN PATENT DOCUMENTS

| | | | | |
|---|---|---|---|---|
| EP | 1 775 298 | | | 4/2007 |
| WO | WO 02/22592 | A2 | | 3/2002 |
| WO | WO 03040131 | | * | 5/2003 |
| WO | WO 2004/007499 | A1 | | 1/2004 |
| WO | WO 2004074283 | | * | 9/2004 |
| WO | WO 2005/014589 | | | 2/2005 |
| WO | WO 2005066145 | | * | 7/2005 |
| WO | WO 2006/004040 | A1 | | 1/2006 |

OTHER PUBLICATIONS

Scozzafava et al. Expert Opinion in Therapeutic Patents, 2004, 14(5), 667-702.*

Gordon et al. American Journal of Psychiatry, 1999, 156(6), 968-969.*

European Office Action dated Oct. 8, 2008.

* cited by examiner

*Primary Examiner*—James O Wilson
*Assistant Examiner*—Noble Jarrell
(74) *Attorney, Agent, or Firm*—Crowell & Moring LLP

(57) ABSTRACT

The present invention relates to novel N-sulfamoyl-piperidineamides of Formula I and their physiologically acceptable acid addition salts, to pharmaceutical compositions comprising them, processes for their preparation, and their use for the treatment of obesity and its concomitant and/or secondary diseases and related or other conditions.

I

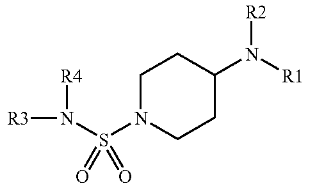

18 Claims, No Drawings

N-SULFAMOYL-PIPERIDINEAMIDES FOR THE TREATMENT OR INHIBITION OF OBESITY AND RELATED CONDITIONS

CROSS-REFERENCE TO RELATED APPLICATIONS

This application claims the benefit under 35 U.S.C. §119 (e) to U.S. provisional patent application Ser. No. 60/749,127 filed Dec. 9, 2005, the entire disclosure of which is hereby incorporated in its entirety.

BACKGROUND OF THE INVENTION

The present invention relates to novel N-sulfamoyl-piperidineamides and their physiologically acceptable acid addition salts, to pharmaceutical compositions comprising them, processes for their preparation, and their use for the treatment of obesity and related conditions.

WO 03/088908 discloses N-sulfamoyl-piperidineamides with a specific substitution pattern at the piperidine ring. The compounds of WO03/088908 are assumedly useful for treating arrhythmia, $I_{Kur}$-associated conditions, gastrointensinal disorders, diabetes, cognitive disorders, and related conditions.

US2004/0167185 describes several N-sulfamoyl-piperidineamides in the area of treating or preventing cancer.

A method of discovering compounds suitable for the treatment and/or prophylaxis of obesity by inhibiting lipogenesis via the inhibition of carbonic anhydrases in mammals and humans is known from document WO 02/07821.

It was an object of the present invention to provide novel medicaments for the treatment and/or prophylaxis of obesity and its concomitant and/or secondary diseases or conditions, which are very effective and can be obtained in simple manner.

It has now surprisingly been found that certain novel N-sulfamoyl-piperidineamides and their physiologically acceptable acid addition salts are suitable for the treatment and/or prophylaxis of obesity and its concomitant and/or secondary diseases or conditions.

The invention is directed to compounds of Formula I,

I

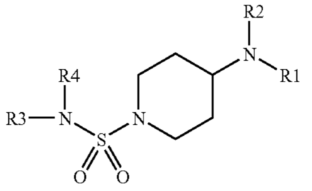

wherein R1 is selected from the group consisting of H; alkyl; cycloalkyl; alkylenealkoxy; alkylenecycloalkyl; aryl unsubstituted or substituted by one or more alkyl, alkoxy, halogen, $CF_3$, CN; alkylenearyl; alkylenearylenealkyl; alkylenearylenehalogen; alkylenearyleneoxyalkyl; alkylenearylenedialkylamin; heteroaryl; alkyleneheteroaryl unsubstituted or substituted with alkyl, alkoxy, halogen, CN, $CF_3$;

wherein R2 is selected from the group consisting of cycloalkyl; aryl unsubstituted or substituted with alkyl, alkoxy, halogen, CN, $CF_3$; alkylenearyl, unsubstituted or substituted, but not substituted by furan or furanyl; alkylenealkoxy; alkylenecycloalkyl; heteroaryl; CO-alkyl; CO-cycloalkyl; CO-aryl substituted by alkyl, alkoxy, halogen, $CF_3$, CN; CO-alkylenearyl unsubstituted or substituted with alkyl, alkoxy, halogen, $CF_3$, CN; CO-heteroaryl unsubstituted or substituted by alkyl, alkoxy, halogen, $CF_3$, CN; CO—O-alkyl; CO—O-cycloalkyl; CO—O-aryl substituted with alkyl, alkoxy, halogen, CN, $CF_3$; CO—O-alkylenearyl unsubstituted or substituted with alkyl, alkoxy, halogen, CN, $CF_3$; CO—O-heteroaryl; CO—NH-alkyl; CO—NH-cycloalkyl; CO—NH-aryl substituted with alkyl, alkoxy, halogen, CN, $CF_3$; CO—NH-alkylenearyl unsubstituted or substituted with alkyl, alkoxy, halogen, CN, $CF_3$; CO—NH-heteroaryl; $SO_2$—$NH_2$; $SO_2$-alkyl; $SO_2$-aryl unsubstiuted or substituted by alkyl, alkoxy, halogen, $CF_3$, CN;

or; wherein R1 and R2 together form a 5 or 6-membered ring which may optionally contain from 1 to 2 additional heteroatoms independently selected from the group consisting of nitrogen, oxygen and sulfur; and which may optionally bear 1 or 2 double bonds; and which may also be substituted by alkyl, halogenalkyl, aryl unsubstituted or substituted with alkyl, alkoxy, hydroxy, halogen, CN, $CF_3$, and/or heteroaryl; and which may also contain a carbonyl group; and which may also be condensed with aryl;

wherein R3 and R4 are independently selected from the group consisting of H, alkyl, cycloalkyl, cycloalkyl containing 1 or more heteroatoms selected from nitrogen and oxygen; cycloalkyl containing 1 or more heteroatoms selected from nitrogen and oxygen, and optionally substituted with alkyl, alkoxy, halogen, $CF_3$, CN; aryl; aryl substituted with alkyl, alkoxy, halogen, $CF_3$, CN; heteroaryl unsubstiututed or substituted with alkyl, alkoxy, halogen, $CF_3$, CN; alkylenearyl; or wherein R3 and R4 together form a 5 or 6-membered ring which may optionally contain from 1 to 2 heteroatoms independently selected from the group consisting of nitrogen and oxygen atoms and which may also be substituted by aryl or aryl substituted with alkyl, alkoxy, halogen, $CF_3$ and CN;

and their physiologically acceptable acid addition salts.

Compounds of Formula I are suitable for the treatment and/or prophylaxis of glaucoma, epilepsy, bipolar disorders, migraine, neuropathic pain, obesity, type II diabetes, metabolic syndrome, alcohol dependence, and/or cancer, and its concomitant and/or secondary diseases or conditions in mammals and humans.

More specifically, in compounds of Formula I, R1 is selected from the group consisting of H; alkyl; cycloalkyl; alkylenealkoxy; alkylenecycloalkyl; aryl; alkylenearyl; heteroaryl; alkyleneheteroaryl unsubstituted or substituted with halogen; R2 is selected from the group consisting of cycloalkyl; aryl substituted with alkyl, alkoxy, halogen, CN, $CF_3$; alkylenearyl, unsubstituted or substituted, but not substituted by furan or furanyl; alkylenealkoxy; alkylenecycloalkyl; CO-alkyl; CO-cycloalkyl; CO-alkylenearyl; CO-heteroaryl; CO—O-alkyl; CO—O-cycloalkyl; CO—O-aryl substituted with alkyl, alkoxy, halogen, CN, $CF_3$; CO—O-alkylenearyl unsubstituted or substituted with alkyl, alkoxy, halogen, CN, $CF_3$; CO—O-heteroaryl; CO—NH-aryl substituted with alkyl, alkoxy, halogen, CN, $CF_3$; CO—NH-alkylenearyl unsubstituted or substituted with alkyl, alkoxy, halogen, CN, $CF_3$; CO—NH-heteroaryl; $SO_2$—$NH_2$; or; R1 and R2 together form a 5 or 6-membered ring which may optionally contain from 1 to 2 heteroatoms independently selected from the group consisting of nitrogen, oxygen and sulfur; and which may optionally bear 1 or 2 double bonds; and which may also be substituted by alkyl, halogenalkyl, aryl unsubstituted or substituted with alkyl, alkoxy, hydroxy, halogen, CN, $CF_3$, and/or heteroaryl; and which may also contain a carbonyl group; and which may also be condensed with aryl; R3 and R4 are independently selected from the group consisting of H, alkyl, cycloalkyl; or R3 and R4 together form a 5 or 6-membered ring which may optionally contain from 1 to 2 heteroatoms independently selected from the group consisting of nitrogen and oxygen atoms and which may also be substituted by aryl.

Even more specifically, in compounds of Formula I R1 is selected from the group consisting of H, alkyl; cycloalkyl; alkylenealkoxy; alkylenecycloalkyl; aryl; alkylenearyl; heteroaryl; alkyleneheteroaryl substituted with halogen; R2 is selected from the group consisting of alkylenealkoxy; alkylenecycloalkyl; CO-alkyl; CO-cycloalkyl; CO-alkylenearyl; CO-heteroaryl; CO—NH-alkylenearyl; CO—NH-aryl substituted with alkyl, alkoxy, halogen, CN, $CF_3$; CO—NH-alkylenearyl substituted with alkyl, alkoxy, halogen, CN, $CF_3$; CO—NH-heteroaryl; $SO_2$—$NH_2$; or; R1 and R2 together form a 5 or 6-membered ring which may optionally contain from 1 to 2 heteroatoms independently selected from the group consisting of nitrogen, oxygen and sulfur; and which may optionally bear 1 or 2 double bonds; and which may also be substituted by alkyl, halogenalkyl, aryl unsubstituted or substituted with alkyl, alkoxy, hydroxy, halogen, CN, $CF_3$, and/or heteroaryl; and which may also contain a carbonyl group; and which may also be condensed with aryl; R3 and R4 are independently selected from the group consisting of H, alkyl, cycloalkyl; or R3 and R4 together form a ring selected from the group consisting of pyrrolidinyl, piperidinyl-p-phenyl, piperazinyl-p-phenyl and morpholino.

In a particularly preferred embodiment of the present invention, R1 is only H if R2 does not contain a CO group.

In another particularly preferred embodiment of the present invention, R3 and R4 are both H.

Where in the compounds of Formula I or in other compounds described within the scope of the present invention substituents are or contain alkyl, cycloalkyl, alkylene, alkoxy, these may each be straight-chain or branched and possess 1 to 8, preferably 1 to 6 and more preferably 1 to 4 carbon atoms. Suitable are methyl, ethyl, propyl, iso-propyl, butyl, isobutyl, tert.-butyl, cyclopropyl, cyclobutyl, cyclopentyl, cyclohexyl, methylene, ethylene, propylene, iso-propylene, butylenes, iso-butylene, tert-butylene, methoxy, ethoxy, propoxy, iso-propoxy, butoxy, iso-butoxy, and tert.-butoxy.

Where substituents in compounds of Formula I stand for halogen, fluorine, chlorine, bromine or iodine are suitable. Chlorine and bromine are preferred.

Where substituents in compounds of Formula I stand for aryl single aromatic ring systems with an adequate number of hydrogen atoms dependent upon the substitution pattern are meant. However, condensed and spiro aryl systems are also included in this definition. Suitable aryl substituents are phenyl, 1H-indene, 9H-fluorene, naphthalene, anthracene, and phenathrene.

Where substituents in compounds of Formula I stand for heteroaryl, aryl ring systems are meant wherein one or more carbon atoms from the aromatic ring system are replaced by a heteroatom selected from the group consisting of oxygen, nitrogen and sulfur. Suitable heteroaryls are pyrrol, furane, thiophene, indolizine, indole, isoindole, cumarone, thionaphthene, pyrozole, imidozole, oxazole, isooxazole, thiazole, isothiazole, triazole, tetrazole, thiadiazole, pyridine, pyrane, thiopyrane, chinoline, isochinoline, pyridazine, pyrimidine, pyrazine, and triazine.

Physiologically compatible acid addition salts of compounds of Formula I are their conventional salts with inorganic acids, for example sulfuric acid, phosphoric acids or hydrohalic acids, preferably hydrochloric acid, or with organic acids, for example lower aliphatic monocarboxylic, dicarboxylic or tricarboxylic acids such as maleic acid, fumaric acid, lactic acid, tartaric acid, citric acid, or with sulfonic acids, for example lower alkanesulfonic acids such as methanesulfonic acid or trifluoromethanesulfonic acid, or benzenesulfonic acids optionally substituted in the benzene ring by halogen or lower alkyl, such as p-toluenesulfonic acid. Hydrochloric acid salts of the compounds of Formula I are preferred.

Compounds of Formula I, wherein R3 and R4 are both not H, and their physiologically acceptable acid addition salts can be prepared by reacting a compound of Formula II

II

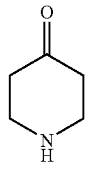

with a sulfamoylchloride of Formula III,

III

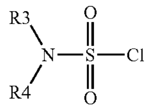

to give compound of Formula IV

IV

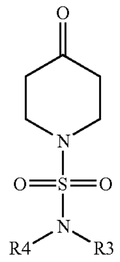

Compounds of Formula IV are then reacted with an amine $H_2NR1$ to give compounds of Formula V

V

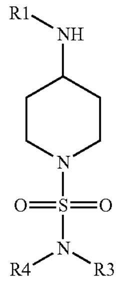

Compounds of Formula V are further reacted with R2X wherein X is selected from the group consisting of Cl, Br, and I, to give compounds of Formula I

I

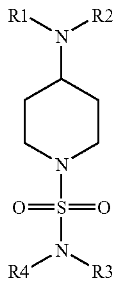

Alternatively, compounds of Formula I wherein R3 and R4 are both not H, can be prepared by reacting compounds of Formula IV with an amine HNR1R2 to give compounds of Formula I

I

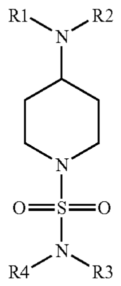

Compounds of Formula I wherein R3 and R4 are both H, can be prepared by reacting a compound of Formula II

II

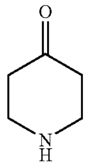

with sulfamoylchloride, which is protected with a protecting group PG, preferably tert.-butyloxycarbonyl or benzyl, of Formula VIa, or with the reagent of Formula VIb, VIa

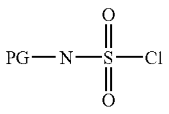

VIb

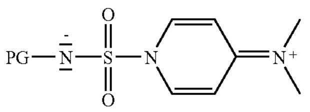

to give a compound of formula VII

VII

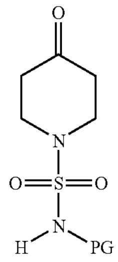

Compounds of Formula VII are then reacted with an amine $H_2NR1$ to give compounds of Formula VIII

VIII

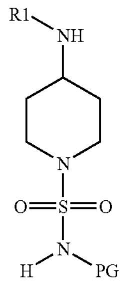

Compounds of Formula VIII are further reacted with R2X wherein X is selected from the group consisting of Cl, Br, and I, to give compounds of Formula IX

IX

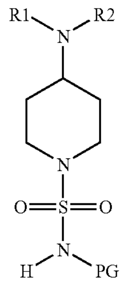

and subsequently cleaving off the protecting group PG under suitable conditions from the obtained intermediate products, then leads to compounds of Formula I wherein R3 and R4 both H. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

Alternatively, compounds of Formula I wherein R3 and R4 are both H, can be prepared by reacting a compound of Formula VII with an amine HNR1R2 to give compounds of Formula IX

IX

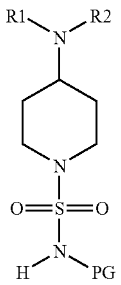

and subsequently cleaving off the protecting group PG under suitable conditions from the obtained intermediate products, then leads to compounds of Formula I wherein R3 and R4 both H. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

Compounds of Formula I wherein R2 contains a methylene spacer $CH_2$, can be prepared by reacting a compound of Formula X

X

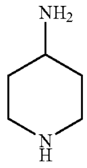

with a protecting agent PG, to give a compound of formula XI

XI

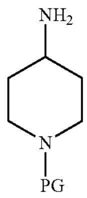

Compounds of Formula XI are then reacted with an aldehyde R2'-CHO, to give compounds of Formula XII,

XII

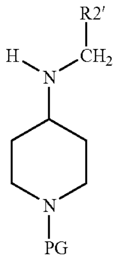

wherein R2' is selected from the group consisting of alkyl; cycloalkyl; alkylenearyl, unsubstituted or substituted, but not substituted by furan or furanyl; alkylenealkoxy; and alkylenecycloalkyl;

Then, the protecting group PG of compounds of Formula XII is cleaved off under suitable conditions and the unprotected compound is then reacted with sulfamoylchloride $ClSO_2—NH_2$ to give compounds of Formula I. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

Alternatively, compounds of Formula I wherein R2 contains a methylene spacer $CH_2$, can be prepared by cleaving off the protecting group PG of compounds of Formula XII under suitable conditions and the then unprotected compound is reacted with sulfamoylchloride, which is protected with a protecting group PG, preferably tert.-butyloxycarbonyl or benzyl, of Formula VIa, or with the reagent of Formula VIb, VIa

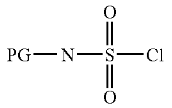

VIb

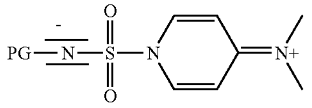

to give a compound of formula XIII

XIII

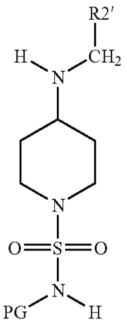

and subsequently cleaving off the protecting group PG under suitable conditions from the obtained intermediate product, then leads to compounds of Formula I wherein R3 and R4 both H. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

In another alternative, compounds of Formula I wherein R2 contains a methylene spacer CH2, can be prepared by reacting a compound of Formula X

X

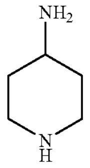

with a protecting agent PG, to give a compound of formula XI

XI

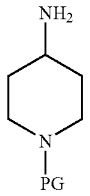

Compounds of Formula XI are then reacted with a ketone R2'-COR1', to give compounds of Formula XIV,

XIV

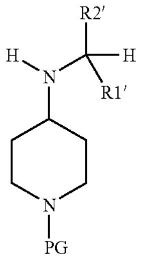

wherein R1' is selected from the group consisting of alkyl; alkylenealkoxy; alkylenecycloalkyl; alkylenearyl; alkylenearylenealkyl; alkylenearylenehalogen; alkylenearyleneoxyalkyl, alkylenearylenedialkylamin; and alkyleneheteroaryl unsubstituted or substituted with alkyl, alkoxy, halogen, CN, $CF_3$;

wherein R2' is selected from the group consisting of alkyl; cycloalkyl; alkylenearyl, unsubstituted or substituted, but not substituted by furan or furanyl; alkylenealkoxy; and alkylenecycloalkyl;

The protecting group PG of compounds of Formula XIV is then cleaved off under suitable conditions and the then unprotected compound is reacted with sulfamoylchloride, which is protected with a protecting group PG, preferably tert.-butyloxycarbonyl or benzyl, of Formula VIa, or with the reagent of Formula VIb, VIa

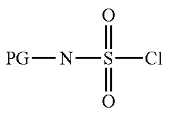

-continued

VIb

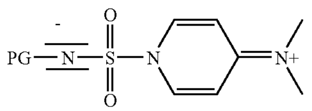

to give a compound of formula XV

XV

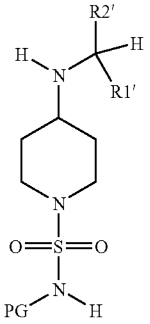

and subsequently cleaving off the protecting group PG under suitable conditions from the obtained intermediate product, then leads to compounds of Formula I wherein R3 and R4 both H. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

Compounds of Formula I can also be prepared by reacting a compound of Formula II

II

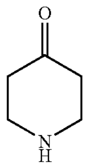

with a protecting agent PG to give a compound of formula XVII

XVII

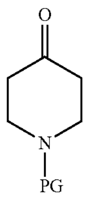

Compounds of Formula XVII are then reacted with an amine NHR1R2 to give compounds of Formula XVIII,

XVIII

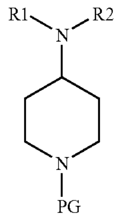

The protecting group PG of compounds of Formula XVIII is then cleaved off under suitable, conditions and the then unprotected compound is reacted with sulfamide to give compounds of Formula I, or with a compound of formula III to give compounds of Formula I, or with a compound of formulae VIa or VIb to give a compound of formula XIX

XIX

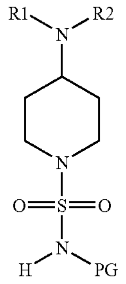

and subsequently cleaving off the protecting group PG under suitable conditions from the obtained intermediate product, then leads to compounds of Formula I. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

In another embodiment compounds of Formula I are prepared by reacting a compound of Formula VXIIIa wherein R1 is H XVIIIa

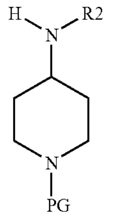

with a compound of formula XX

R5-N═C═O XX wherein R5 is selected from the group consisting of alkyl; cycloalkyl; aryl substituted with alkyl, alkoxy, halogen, CN, $CF_3$; alkylenearyl unsubstituted or substituted with alkyl, alkoxy, halogen, CN, $CF_3$; and heteroaryl; to give a compound of formula XXI

XXI

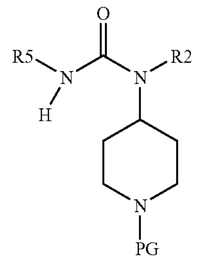

The protecting group PG of compounds of Formula XXI is then cleaved off under suitable conditions and wherein the unprotected compound is then reacted with sulfamide to give compounds of Formula I, or with a compound of formula III to give compounds of Formula I, or with a compound of formulae VIa or VIb to give a compound of formula XXII

XXII

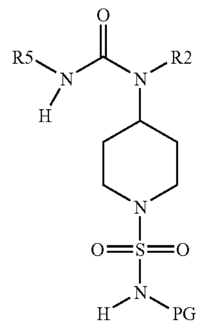

and subsequently cleaving off the protecting group PG under suitable conditions from the obtained intermediate product, then leads to compounds of Formula I. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

Compounds of Formula I can alternatively also be prepared by reacting a compound of Formula VXIIIa wherein R1 is H XVIIIa

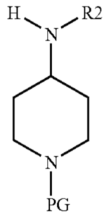

with a compound of formula XXIII

XXIII

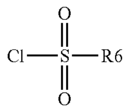

wherein R6 is selected from the group consisting of alkyl; aryl unsubstiuted or substituted by alkyl, alkoxy, halogen, $CF_3$, CN; to give a compound of formula XXIV

XXIV

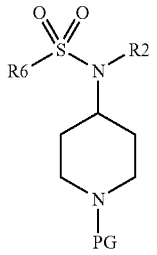

The protecting group PG of compounds of Formula XXIV is then cleaved off under suitable conditions and wherein the unprotected compound is then reacted with sulfamide to give compounds of Formula I, or with a compound of formula III to give compounds of Formula I, or with a compound of formulae VIa or VIb to give a compound of formula XXV

XXV

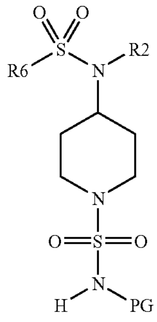

and subsequently cleaving off the protecting group PG under suitable conditions from the obtained intermediate product, to give compounds of formula I. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

In another embodiment of the present invention, compounds of Formula I can be prepared by reacting a compound of Formula XI

XI

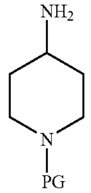

with a compound of formula XXIII to give compounds of Formula XXVI

XXVI

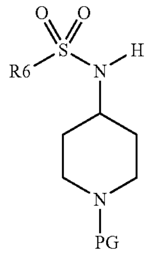

The protecting group PG of compounds of Formula XXVI is then cleaved off under suitable conditions and wherein the unprotected compound is then reacted with sulfamide to give compounds of Formula I, or with a compound of formula III to give compounds of Formula I, or with a compound of formulae VIa or VIb to give a compound of formula XXVII

XXVII

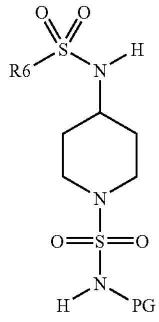

and subsequently cleaving off the protecting group PG under suitable conditions from the obtained intermediate product, to give compounds of formula I. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

In another embodiment of the present invention, compounds of Formula I can be prepared by reacting a compound of Formula VIII

VIII

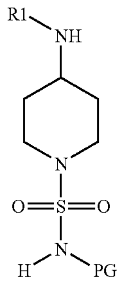

with compounds of formula XX

R5-N═C═O XX to give compounds of Formula XXVIII

XXVIII

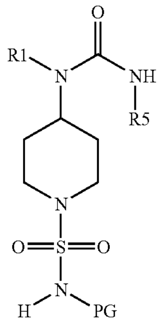

The protecting group PG of compounds of Formula XXVIII is then cleaved off under suitable conditions to give compounds of Formula I. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

In another embodiment of the present invention, compounds of Formula I can be prepared by reacting a compound of Formula XI

XI

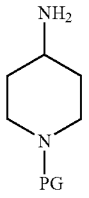

with compounds of formula XXIX

XXIX

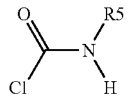

to give compounds of Formula XXX

XXX

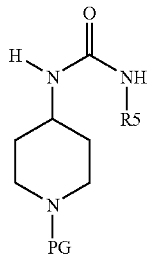

The protecting group PG of compounds of Formula XXX is then cleaved off under suitable conditions to give compounds of Formula XXXI

XXXI

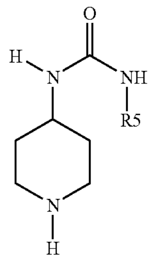

Further on, the compound of Formula XXXI is then reacted with sulfamoylchlorid of Formula III to give compounds of Formula I, or the compound of Formula XXXI is then reacted with a compound of Formulae VIa or VIb to give a compound of Formula XXXII

XXXII

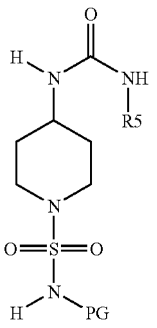

The protecting group PG of compounds of Formula XXXII is then cleaved off under suitable conditions to give compounds of Formula I. If the protecting group is tert.-butyloxycarbonyl, then the removal of PG can be achieved under acidic conditions, preferably in the presence of hydrogen chloride. If the protecting group is benzyl, then the removal of PG can be achieved with hydrogenation, preferably in the presence of hydrogen and a catalyst, such as Pd.

If desired, the resulting free bases of compounds of Formula I independently of their substitution pattern at R3 and R4 can be converted into their physiologically acceptable acid addition salts, or, the resulting acid addition salts of the compounds of Formula I independently of their substitution pattern at R3 and R4, can be converted into the free bases of Formula I.

In yet another aspect, the present invention also relates to a method of treating or preventing glaucoma, epilepsy, bipolar disorders, migraine, neuropathic pain, obesity, type II diabetes, metabolic syndrome, alcohol dependence, and/or cancer, and its concomitant and/or secondary diseases or conditions in mammals and humans, comprising administering to a subject in need thereof a therapeutically effective amount of a compound of Formula I or its physiologically compatible acid addition salts.

Obesity according to the present invention is meant to comprise any increase in body fat that results in increased bodyweight, comprising as a preferred alternative but not limited to the medical definition of obesity. The invention thus also relates to non-medical weight loss, such as cosmetic weight loss and includes improving bodily appearance in general. Further, the term obesity also is meant to comprise drug induced obesity and/or juvenile obesity.

The concomitant diseases of obesity and its concomitant and/or secondary diseases or conditions in mammals and humans according to the invention include in particular the metabolic syndrome and/or syndrome X and cardiovascular diseases.

The term "metabolic syndrome" as used in this application is meant to cover a complex of clinical pictures which—besides central obesity—mainly comprises hypertension, in particular arterial hypertension; insulin resistance, in particular diabetes mellitus type II; glucose intolerance; dyslipoproteinaemia, in particular as hypertriglyceridaemia, accompanied by dyslipoproteinaemia occurring with lowered HDL-cholesterol, and also hyperuricaemia, which can lead to gout. According to information from the American Heart Association, the metabolic syndrome is closely linked to insulin resistance. Some people are genetically predisposed to insulin resistance. Acquired factors, such as excess body fat and physical inactivity, can elicit insulin resistance and the metabolic syndrome in these people. Most people with insulin resistance have central obesity. The biologic mechanisms at the molecular level between insulin resistance and metabolic risk factors are not fully understood and appear to be complex. One group of people at risk for developing metabolic syndrome are those with diabetes who have a defect in insulin action and cannot maintain a proper level of glucose in their blood. Another is people, mainly those with high blood pressure, who are nondiabetic and insulin-resistant but who compensate by secreting large amounts of insulin. This condition is known as hyperinsulinemia. A third group is heart attack survivors who, unlike hypertensives, have hyperinsulinemia without having abnormal glucose levels. The metabolic syndrome has become increasingly common in higher developed countries like the United States, where it is estimated that about 20-25 percent of US adults have it. There are no well-accepted criteria for diagnosing the metabolic syndrome.

The criteria proposed by the Third Report of the National Cholesterol Education Program (NCEP) Expert Panel on Detection, Evaluation, and Treatment of High Blood Cholesterol in Adults (Adult Treatment Panel III) are the most current and widely used. According to the ATP III criteria, the metabolic syndrome is identified by the presence of three or more of these components:

Central obesity as measured by waist circumference (Men—Greater than 40 inches; Women—Greater than 35 inches).

Fasting blood triglycerides greater than or equal to 150 mg/dL.

Blood HDL cholesterol (Men—Less than 40 mg/dL; Women—Less than 50 mg/dL)

Blood pressure greater than or equal to 130/85 mmHg.

Fasting glucose greater than or equal to 110 mg/dL.

The term "syndrome X" is closely related to the term "metabolic syndrome" and usually is supposed to denominate the identical disease or condition. According to information from the American Heart Association, the term "Syndrome X" refers, however, additionally to a heart condition where chest pain and electrocardiographic changes that suggest ischemic heart disease are present, but where there are no angiographic findings of coronary disease. Patients with cardiac syndrome X also sometimes have lipid abnormalities.

The term "cardiovascular diseases" in conjunction with obesity is usually understood to mean coronary heart disease, which can lead to heart failure, cerebrovascular diseases, which may for example be accompanied by an increased risk of strokes, and peripheral occlusive arterial disease.

Due to their inherent properties, the compounds of Formula I or their physiologically compatible acid addition salts are also expected to be useful in the treatment of diabetic conditions or diseases which are unrelated to obesity. Such diabetic conditions or diseases comprise e.g. diabetes mellitus type II, diabetic neuropathy, diabetic retinopathy, diabetic nephropathy, diabetic microangiopathy or diabetic macroangiopathy.

Further concomitant and/or secondary diseases of obesity may be gall-bladder diseases such as formation of gallstones, sleep apnoea syndrome, orthopaedic complications such as osteoarthritis and psychosocial disorders.

The compounds of Formula I are further deemed to be useful as anticonvulsants for the prophylaxis or treatment of epilepsy in mammals and humans.

The compounds of Formula I according to the invention are inhibitors of mammalian carbonic anhydrases, in particular of human carbonic anhydrase isozymes of subtypes II and/or V (=hCA II and/or hCA V).

Pharmacological Test Methods

The example numbers quoted in the pharmacological test methods relate to the preparation examples described below.

1. In Vitro Inhibition of Human Carbonic Anhydrase Isoenzyme II (hCA II)

The test compounds of Formula I in 96 well microplates were diluted with aqua bidest by using an automatic pipettor (CyBiWell®). From the different dilution plates, aliquots of 20 µl were transferred to the 96 well black assay plates with a pipetting station (Tecan Genesis®). In a second step, 148 µl of potassium phosphate buffer (20 mM, pH 7.4) was added, and as a third step, 20 µl of enzyme solution (1 µM human carbonic anhydrase isoenzyme II from erythrocytes (Sigma-Aldrich), dissolved in potassium phosphate buffer) incubated for 60 min at room temperature and the fluorescence signal (Tecan Ultra® fluorescence reader; excitation wavelength: 280 nm; emission wavelength: 465 nm) read at the end of the preincubation period (FLU-1). After the preincubation time, 20 µl of aqueous dansylamide solution (1 mM dansylamide (Sigma-Aldrich), dissolved in hydrochloric acid) were added and the fluorescence signal read every 10 min for a period of 60 min at 37° C. For calculation, the fluorescence data of the time point 60 min (FLU-2) were used. The total volume of assay mixture amounted to 208 μl. The final concentration of carbonic anhydrase II was $10^{-7}$ M/L, of dansylamide $2.25\times10^{-6}$ and of compounds from $10^{-8}$ M/L up to $10^{-5}$ M/L. Final concentration of DMSO as compound solvent was 0.1 mM. Each microplate also contained blanks without compound and enzyme, controls without compound and ethoxzolamide (final concentration $5\times10^{-8}$ M/L). All data reflect single measurements. Data were expression as % inhibition after calculation by the formula:

$$\%\ \text{inhibition}=100((1-(\text{FLU-2}_{cpd}-\text{FLU-2}_{blank}-\text{FLU-1}_{cpd}+\text{FLU-1}_{blank})/(\text{FLU-2}_{control}-\text{FLU-2}_{blank}-\text{FLU-1}_{control}-\text{FLU-1}_{blank}))$$

The % inhibiton data for each compound and the respective final concentration were used for $IC_{50}$ calculations by using the Prism 4 software. Concentration action figures were calculated by applying the Prism algorithm for nonlinear regression (curve-fit): sigmoidal dose response with variable slope and the constraints: top: 100 and bottom 0.

In this test substances of Formula I listed in Table 1 below showed the $IC_{50}$ values given below:

TABLE 1 hCA II inhibiting effect of the test substances in vitro

| Example No. | $IC_{50}$ [μM] |
|---|---|
| 9 | 7.2 |
| 10 | 7.3 |
| 11 | 6.5 |
| 28 | 6.6 |

2. Acute In Vivo Food Intake Test in Mice

The studies were carried out in male or female C57B1/6 mice (n=8-12 per group). The mice were kept on an inverted 12/12h light/dark cycle (lights on 22:00). They were allowed food (high caloric diet) and water ad libitum. Food intake and water consumption was measured daily. The test compound of Formula I was suspended in 1% methylcellulose in water and 2% (v/v) of Poloxamer 188 (Lutrol F68®) and administered by oral gavage at a dose of 100 mg/kg/day. One half of the dose was administered at 7.00-9.00 h; the remaining half of the dose was administered between 15.00-15.30 h.

In the test model described above, the test substances caused a decrease of the animals' 24 h food intake to the percentages of food intake when compared to control as given in the following Table 2.

TABLE 2

Influence of test substances on food intake

| Example No. | food intake [% of control] |
|---|---|
| 1 | 83 |
| 17 | 84 |
| 19 | 93 |
| 26 | 63 |

The present invention further provides a pharmaceutical composition or medicament comprising a pharmacologically effective quantity of a compound of Formula I or its physiologically compatible acid addition salts and further comprising conventional pharmaceutically acceptable auxiliaries Suitable pharmaceutically acceptable auxiliaries and/or carriers are well know in the art and include pharmaceutical grade starch, mannitol, lactose, magnesium stearate, sodium saccharin, talcum, cellulose, glucose, sucrose (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration). The compounds according to the invention or their physiologically compatible acid additions salts for use in the aforementioned indications may be administered by any convenient method, for example by oral (including by inhalation), parenteral, mucosal (e.g. buccal, sublingual, nasal), rectal or transdermal administration and the compositions adapted accordingly. For oral administration, the compounds can be formulated as liquids or solids, for example solutions, syrups, suspensions or emulsions, tablets, capsules and lozenges. A liquid formulation will generally consist of a suspension or solution of the compound or physiologically acceptable salt in a suitable aqueous or non-aqueous liquid carrier(s) for example water, ethanol, glycerine, polyethylene glycol or an oil.

The formulation may also contain a suspending agent, preservative, flavouring or coloring agent. A composition in the form of a tablet can be prepared using any suitable pharmaceutical carrier(s) routinely used for preparing solid formulations. Examples of such carriers include magnesium stearate, starch, lactose, sucrose and microcrystalline cellulose. A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule. Compositions for oral administration may be designed to protect the active ingredient against degradation as it passes through the alimentary tract, for example by an outer coating of the formulation on a tablet or capsule. Typical parenteral compositions consist of a solution or suspension of the compound or physiologically compatible acid addition salts in a sterile aqueous or non-aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration. Compositions for nasal or oral administration may conveniently be formulated as aerosols, drops, gels and powders.

Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser. Compositions suitable for buccal or sublingual administration include tablets, lozenges and pastilles, wherein the active ingredient is formulated with a carrier such as sugar and acacia, tragacanth, or gelatin and glycerin. Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections. Conveniently the composition is in unit dose form such as a tablet, capsule or ampoule. The pharmaceutical compositions according to the invention are useful in the prevention and/or treatment of obesity, concomitant and/or secondary diseases of obesity; other medical weight loss and non-medical related weight loss; and/or diabetic conditions or diseases.

The compounds of the present invention and their physiologically compatible acid addition salts are generally administered as pharmaceutical compositions which are important and novel embodiments of the invention because of the presence of the compounds disclosed herein. In embodiments of the invention, a pharmaceutical pack or kit is provided comprising one or more container(s) filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Yet a further aspect of the invention provides a process for the manufacture of a pharmaceutical composition as described hereabove. The manufacture can be carried out by standard techniques well known in the art and involves combining a compound according to the invention and the pharmaceutically acceptable auxiliaries and/or carriers. The composition may be in any form including a tablet, a liquid, a capsule, and a powder or in the form of a food product, e.g. a functional food. In the latter case the food product itself may act as the pharmaceutically acceptable carrier.

The compound or composition is preferably administered to a patient in need thereof and in a quantity sufficient to prevent and/or treat the symptoms of the condition, disorder or disease. For all aspects of the invention, particularly medical ones, the administration of a compound or composition has a dosage regime which will ultimately be determined by the attending physician and will take into consideration such factors such as the compound being used, animal type, age, weight, severity of symptoms, method of administration, adverse reactions and/or other contraindications. Specific defined dosage ranges can be determined by standard design clinical trials with patient progress and recovery being fully monitored. Such trials may use an escalating dose design using a low percentage of the maximum tolerated dose in animals as the starting dose in man. The physiologically acceptable compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the Formula I or a physiologically acceptable salt thereof calculated as the free base, the compound being administered 1 to 4 times per day. The compound used according to the invention can also be administered to children or juveniles while the individual dosage regimens in these cases will need to be particularly thoroughly adjusted by the physician and will usually comprise lower doses than will be administered to adults.

Suitably the compounds will be administered for a period of continuous therapy, for example for at least a week, but usually for a longer period of several weeks to several months. The invention also provides a cosmetic method (non-therapeutic) for maintaining a given weight, or for cosmetic weight loss, the method comprising the administration of a compound according to the other aspects of the invention, preferably in combination with a pharmaceutically acceptable carrier or diluent.

The compound or composition is preferably administered to a subject in need or in desideratum thereof and in a quantity sufficient to maintain a given weight or for cosmetic weight loss.

In still a further aspect, the compounds of Formula I and their physiologically compatible acid addition salts may favourably be administered in combination with one or more active agents (as a pharmaceutical combination composition) selected from antidiabetics; antiobesity or appetite-regulating agents; cardiovascular active agents, in particular antihypertensives; diuretics; active agents altering lipid levels, in particular lipid-lowering agents; and active ingredients for the treatment and/or prevention of complications caused by diabetes or associated with diabetes.

Suitable antidiabetics comprise e.g. insulins, amylin, derivatives of GLP-1 and GLP-2 such as, for example, those disclosed in WO 98/08871 and orally active hypoglycemic active ingredients. The orally active hypoglycemic active ingredients preferably comprise sulfonylureas, e.g tolbutamide, glibenclamide, glimepiride, glipizide, gliquidone, glisoxepide, glibomuride or gliclazide; biguanides, e.g. metformin; meglitinides, e.g. repaglinide; beta3 adrenergic agonists; oxadiazolidinediones; glucosidase inhibitors e.g. alpha-glucosidase inhibitors such as miglitol or acarbose; glucagon receptor antagonists, GLP-1 agonists, potassium channel openers like diazoxide or those disclosed in WO 97/26265 or WO 99/03861; CB-1 (cannabinoid-1 receptor) antagonists/inverse agonists; insulin sensitizers like thiazolidinediones, e.g. troglitazone, ciglitazone, pioglitazone, rosiglitazone or the compounds disclosed in WO 97/41097, in particular 5-[[4-[(3,4-dihydro-3-methyl-4-oxo-2-quinazolinylmethoxy]pheny-1]methyl]-2,4-thiazolidine dione; activators of insulin receptor kinase; inhibitors of liver enzymes involved in the stimulation of gluconeogenesis and/or glycogenolysis, for example inhibitors of glycogen phosphorylase; and modulators of glucose uptake and glucose excretion.

Suitable antiobesity or appetite-regulating agents comprise one or more of a 5-HT (serotonin) transporter inhibitor, a NE (norepinephrine) transporter inhibitor, a CB-1 (cannabinoid-1 receptor) antagonist/inverse agonist, a ghrelin antibody, a ghrelin antagonist, a H3 (histamine H3) antagonist/inverse agonist, a MCH1R (melanin concentrating hormone 1R) antagonist, a MCH2R (melanin concentrating hormone 2R) agonist/antagonist, a NPY1 (neuropeptide Y Y1) antagonist, a NPY2 (neuropeptide Y Y2) agonist, a NPY5 (neuropeptide Y Y5) antagonist, leptin, a leptin derivative, an opioid antagonist, an orexin antagonist, a BRS3 (bombesin receptor subtype 3) agonist, a CCK-A (cholecystokinin-A) agonist, a CNTF (ciliary neurotrophic factor), a CNTF derivative, a GHS (growth hormone secretagogue receptor) agonist, SHT2c (serotonin receptor 2c) agonist, a Mc3r (melanocortin 3 receptor) agonist, a Mc4r (melanocortin 4 receptor) agonist, a monoamine reuptake inhibitor, a serotonin reuptake inhibitor, a GLP-1 (glucagon-like peptide 1) agonist, topiramate, phytopharm compound 57, an ACC2 (acetyl-CoA carboxylase-2) inhibitor, a beta3 adrenergic agonist, a DGAT1 (diacylglycerol acyltransferase 1) inhibitor, a DGAT2 (diacylglycerol acyltransferase 2) inhibitor, a FAS (fatty acid synthase) inhibitor, a PDE (phosphodiesterase) inhibitor, a thyroid hormone B agonist, an UCP-1 (uncoupling protein 1), 2, or 3 activator, an acyl-estrogen, a glucocorticoid antagonist, an 11 HSD-1 (11-beta hydroxy steroid dehydrogenase type 1) inhibitor, a SCD-1 (stearoyl-CoA desaturase-1) inhibitor, a dipeptidyl peptidase IV (DP-IV) inhibitor, a lipase inhibitor, a fatty acid transporter inhibitor, a dicarboxylate transporter inhibitor, a glucose transporter inhibitor, a phosphate transporter inhibitor, and pharmaceutically acceptable salts and esters thereof.

Suitable appetite-regulating agents (appetite suppressants) comprise sibutramine or the mono- and bisdemethylated active metabolites of sibutramine; fenfluramine or dexfenfluramine; mazindol, diethylpropion or phentermine; leptin or modified leptin; dexamphetamine and amphetamine.

Suitable lipase inhibitors comprise orlistat, panclicins, lipase inhibitors isolated from micro organisms such as lipstatin (from *Streptomyces toxytricini*), ebelactone B (from *Streptomyces aburaviensis*), synthetic derivatives of these compounds; 2-oxy-4H-3,1-benzoxazin-4-one derivatives like Alizyme's ATL-962 or structurally related compounds; 2-amino-4H-3,1-benzoxazin-4-one derivatives or extracts of plants known to possess lipase inhibitory activity, e.g. extracts of *Alpinia officinarum* or compounds isolated from such extracts like 3-methylethergalangin (from *A. officinarum*);

Suitable CB1-cannabinoid antagonists include rimonabant, SLV319, SR147778 and CP-945598.

Suitable cardiovascular active agents comprise angiotensin II receptor antagonists, e.g. abitesartan, benzyllosartan, candesartan, elisartan, embusartan, enoltasosartan, eprosartan, fonsartan, forasartan, glycyllosartan, irbesartan, isoteoline, losartan, milfasartan, olmesartan, opomisartan, pratosartan, ripisartan, saprisartan, saralasin, sarmesin, tasosartan, telmisartan, valsartan, zolasartan; Kissei KRH-94, Lusofarmaco LR-B/057, Lusofarmaco LR-B/081, Lusofarmaco LR B/087, Searle SC-52458, Sankyo CS-866, Takeda TAK-536, Uriach UR-7247, A-81282, A-81988, BIBR-363, BIBS39, BIBS-222, BMS-180560, BMS-184698, CGP-38560A, CGP-48369, CGP-49870, CGP-63170, CI-996, CV-11194, DA-2079, DE-3489, DMP-811, DuP-167, DuP-532, GA-0056, E-4177, EMD-66397, EMD-73495, EXP-063, EXP-929, EXP-3174, EXP-6155, EXP-6803, EXP-7711, EXP-9270, FK-739, HN-65021, HR-720, ICI-D6888, ICI-D7155, ICI-D8731, KRI-1177, KT3-671, KW-3433, L-158809, L-158978, L-159282, L-159689, L-159874, L-161177, L-162154, L-162234, L-162441, L-163007, L-163017, LY-235656, LY-285434, LY-301875, LY-302289, LY-315995, ME-3221, PD-123177, PD-123319, PD-150304, RG-13647, RWJ-38970, RWJ-46458, S-8307, S-8308, SL-91.0102, U-96849, U-97018, UP-269-6, UP-275-22, WAY-126227, WK-1492.2K, WK-1360, X-6803, XH-148, XR-510, YM-358, YM-31472, ZD-6888, ZD-7155 and ZD-8731 or any physiologically compatible salts, solvates, prodrugs or esters thereof; daglutril; non-selective alpha-adrenoceptor antagonists, e.g. tolazoline or phenoxybenzamine; selective alpha-adrenoceptor antagonists, e.g. doxazosin, prazosin, terazosin or urapidil; beta-adrenoceptor antagonists, e.g. acebutolol, alprenolol, atenolol, betaxolol, bisoprolol, bupranolol, carazolol, carteolol, celiprolol, mepindolol, metipranolol, metoprolol, nadolol, oxprenolol, penbutolol, pindolol, propranolol, sotalol and timolol; mixed antagonists of alpha- and beta-adrenoceptors, e.g. carvedilol or labetolol; ganglion blockers, e.g. reserpine or guanethidine; alpha2-adrenoceptor agonists (including centrally acting alpha2-adrenoceptor agonists), e.g. clonidine, guanfacine, guanabenz methyldopa and moxonidine; renin-inhibitors, e.g. alskiren; ACE-inhibitors, e.g. benazepril, captopril, cilazapril, enalapril, fosinopril, imidapril, lisinopril, moexipril, quinapril, perindopril, ramipril, spirapril or trandolapril; mixed or selective endothelin receptor antagonists e.g. atrasentan, bosentan, clazosentan, darusentan, sitaxsentan, tezosentan, BMS-193884 or J-104132; direct vasodilators, e.g. diazoxide, dihydralazine, hydralazine or minoxidil; mixed ACE/NEP-inhibitors, e.g. omapatrilat; ECE-inhibitors, e.g. FR-901533; PD-069185; CGS-26303; CGS-34043; CGS-35066; CGS-30084; CGS-35066; SM-19712; Ro0677447; selective NEP-inhibitors; vasopressin antagonists, aldosterone receptor antagonists, e.g. eplerenone or spironolactone; angiotensin vaccine; and urotensin II receptor antagonists.

Suitable diuretics comprise thiazide diuretics, e.g. althiazide, bemetizide, bendroflumethiazide, benzylhydrochlorothiazide, benzthiazide, buthiazide, chlorothiazide, cyclothiazide, hydrochlorothiazide, hydroflumethiazide, methyclothiazide, paraflutizide, polythiazide, teclothiazide, trichlormethiazide; thiazide analog diuretics, e.g. chloraminofenamide, chlortalidone, clofenamide, clopamide, clorexolone, fenquizone, indapamide, mefruside, metolazone, quinethazone, tripamide, xipamide; loop diuretics, e.g. azosemide, bumetanide, furosemide, piretanide, torsemide; potassium sparing diuretics, e.g. amiloride, potassium canrenoate, spironolactone, triamterene or any physiologically compatible tautomers, salts, solvates, prodrugs or esters of any afore mentioned diuretic.

Suitable active agents which alter lipid levels comprise compounds which alter lipid metabolism, such as antihyperlipidemic active ingredients and antilipidemic active ingredients like HMGCoA reductase inhibitors, e.g. atorvastatin, berivastatin, cerivastatin, crilvastatin, fluvastatin, glenvastatin, lovastatin, mevastatin, pitavastatin, pravastatin, rosuvastatin, simvastatin or any physiologically compatible salts, solvates, prodrugs or esters thereof; inhibitors of cholesterol transport/of cholesterol uptake; inhibitors of bile acid reabsorption or inhibitors of the microsomal triglyceride transfer protein (MTP); compounds which reduce food intake, PPAR (=peroxisome proliferator-activated receptors) and RXR agonists and active agents which act on the ATP-dependent potassium channel of the beta cells; fibric acids, e.g. bezafibrate, ciprofibrate, clofibrate, fenofibrate or gemfibrozil; cholestyramine, colestipol, probucol, ezetimibe and dextrothyroxine; HMGCoA synthase inhibitor, a cholesterol absorption inhibitor, an acyl coenzyme A-cholesterol acyl transferase (ACAT) inhibitor, a cholesteryl ester transfer protein (CETP) inhibitor, a squalene synthetase inhibitor, an anti-oxidant, a PPAR □ agonist, a FXR receptor modulator, a LXR receptor agonist, a lipoprotein synthesis inhibitor, a renin angiotensin system inhibitor, a microsomal triglyceride transport inhibitor, a bile acid reabsorption inhibitor, a PEAR8 agonist, a triglyceride synthesis inhibitor, a transcription modulator, a squalene epoxidase inhibitor, a low density lipoprotein receptor inducer, a platelet aggregation inhibitor, a 5-LO or FLAP inhibitor, a PPAR 8 partial agonist, and niacin or a niacin receptor agonist, and pharmaceutically acceptable salts and esters thereof.

Further active agents which may be suitable for use in combination with the compound of Formula I according to the present invention may be selected from the group consisting of CART agonists, H3 antagonists, TNF agonists, CRF agonists, CRF BP antagonists, urocortin agonists, beta3-agonists, MSH (melanocyte-stimulating hormone) agonists, serotonin-reuptake inhibitors, mixed serotonin- and noradrenaline-reuptake inhibitors, 5HT modulators, MAO inhibitors, galanin antagonists, growth hormone, growth hormone-releasing compounds, TRH agonists, modulators of uncoupling proteins 2 or 3, leptin agonists, dopamine agonists (bromocriptine, doprexin), RXR modulators, hCNTF agonists and TR-beta-agonists.

Preferred pharmaceutical combination compositions according to the invention comprise combinations of at least one compound of Formula I and at least one biguanide; at least one compound of Formula I and at least one fibric acid; at least one compound of Formula I and at least one HMG-CoA reductase inhibitor; and at least one compound of Formula I and at least one insulin sensitizer.

Preferred compounds of Formula I for combination with one or more of the above mentioned active agents are 4-phenyl-piperazine-1-sulfonic acid amide; 4-(2-chloro-phenyl)-piperazine-1-sulfonic acid amide; 4-(2-methoxy-phenyl)-piperazine-1-sulfonic acid amide; 4-pyridin-4-yl-piperazine-1-sulfonic acid amide; 4-pyrimidin-2-yl-piperazine-1-sulfonic acid amide; 4-(4-fluoro-phenyl)-piperazine-1-sulfonic acid amide; 4-(4-chloro-3-trifluoromethyl-phenyl)-piperazine-1-sulfonic acid amide and/or 4-(3-chloro-5-trifluoromethyl-pyridin-2-yl)-piperazine-1-sulfonic acid amide.

Metformine is the preferred biguanide for combination with at least one compound of Formula I.

Preferred fibric acids for combination with at least one compound of Formula I are bezafibrate, ciprofibrate, clofibrate, fenofibrate and/or gemfibrozil. Fenofibrate is most preferred.

Preferred HMGCoA reductase inhibitors for combination with at least one compound of Formula I are atorvastatin, berivastatin, cerivastatin, crilvastatin, fluvastatin, glenvastatin, lovastatin, mevastatin, pitavastatin, pravastatin, rosuvastatin and/or simvastatin or any physiologically compatible salts, solvates, prodrugs or esters thereof. Most preferred are simvastatin, lovastatin and/or pravastatin.

Preferred insulin sensitizers for combination with at least one compound of Formula I are thiazolidinediones, in particular troglitazone, ciglitazone, pioglitazone and/or rosiglitazone. Rosiglitazone and pioglitazone are most preferred.

More preferred combinations according to the invention are the combinations of 4-phenyl-piperazine-1-sulfonic acid amide with metformine; 4-phenyl-piperazine-1-sulfonic acid amide with fenofibrate; 4-phenyl-piperazine-1-sulfonic acid amide with simvastatin and 4-phenyl-piperazine-1-sulfonic acid amide with rosiglitazone.

In one embodiment of the pharmaceutical combination compositions as described above and according to the invention, the compounds of Formula I can be obtained and administered together with the different active agents, e.g. in one combined unit dosage form like in one tablet or capsule, i.e. in a physical combination. In such a combined unit dosage form, the compound of Formula I and the different active agents can be segregated from each other, e.g. by means of different layers in said tablet, e.g. by using inert intermediate layers known in the art; or by using different compartments in the capsule. The corresponding active agents or their pharmaceutically acceptable salts may also be used in form of their hydrates or include other solvents used for crystallization. A unit dosage form may be a fixed combination. A unit dosage form, in particular a fixed combination of the compound of Formula I and one or more of the different active agents is a preferred alternative of this embodiment.

In another embodiment the compounds of Formula I and the different active agents can be obtained and administered in two or more separate unit dosage forms, e.g. in two or more tablets or capsules, the tablets or capsules being physically segregated from each other. The two or more separate unit dosage forms can be administered simultaneously or stepwise (separately), e.g. sequentially one after the other in either order. Thus, the compounds of Formula I and the different active agents can be administered in either order at the same time or at different times spread over the day, the optimal dosage regimen usually being determined by prescription of a physician.

The following examples are intended to explain the invention further, without limiting its scope.

EXAMPLE 1

Urea-analogs (R1=H, R2=CO—NH—$C_6H_4F$; boc=tert.-butyloxycarbonyl)

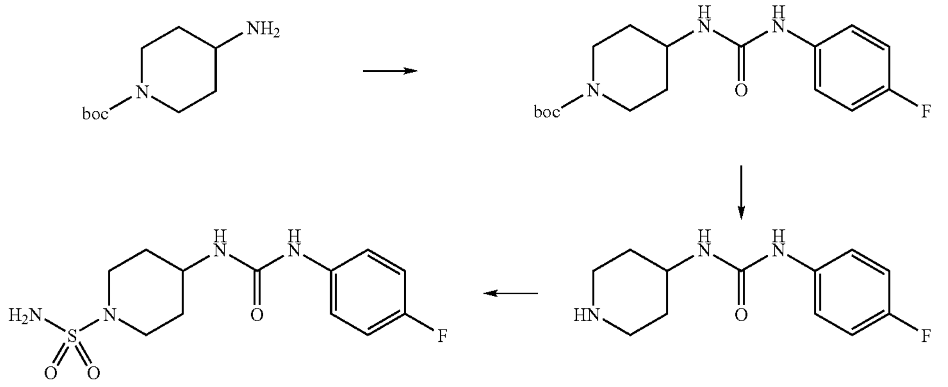

1.1 To an ice-cooled solution of 0.7 g 1-fluoro-4-isocyanato-benzene in 25 ml dichloromethane was added dropwise a solution of 1.0 g tert.-butyl-4-aminopiperidine-1-carboxylate in 25 ml dichloromethane under an atmosphere of nitrogen. This mixture was stirred 10 min. at 0° C. and then 16 hrs. at room temperature. The reaction mixture was diluted with water and then washed with a saturated solution of NaCl in water. After separation the organic layer was dried over sodium sulfate and evaporated under reduced pressure, yielding 1.6 g tert.-butyl-4-{[[(4fluorophenyl)-amino]-carbonyl]amino}-piperidine-1-carboxylate.

$^1$H NMR (δ ppm, 400 MHz): 7.37 [2H], 7.04 [2H], 8.34 [1H, NH], 6.13 [1H, NH], 1.40 [9H].

1.2 1.6 g tert.-butyl-4-{[[(4fluorophenyl)amino]carbonyl]amino}piperidine-1-carboxylate were dissolved in 50 ml dichloromethane. This solution was cooled to 0° C. and then 2.3 ml trifluoroacetic acid were added. After stirring for 40 hrs. at room temperature the reaction mixture was evaporated under reduced pressure and twice treated with toluene. After drying in vacuum 2.4 g of 1-(4-fluorophenyl)-3-piperidine-4-yl-urea as trifluoroacetic acid-salt were obtained.

$^1$H NMR (δ ppm, 400 MHz): 7.39 [2H], 7.05 [2H], 8.51 [1H, NH], 6.56 [1H, NH].

1.3 2.4 g of 1-(4-fluorophenyl)-3-piperidine-4-yl-urea-trifluoroacetic-acid-salt, 7 ml triethylamine and 1.17 g sulfamide were dissolved in 70 ml dioxane and refluxed (130° C.) for 5 hrs. After removal of the solvent under reduced pressure the crude product was purified by flash-chromatography using a 9:1 mixture of dichloromethane/methanol as eluent. 1.0 g 4-{[[(4fluorophenyl)amino]-carbonyl]amino}piperidine-1-sulfonamide, melting point 219.6-221.2° C., were obtained.

EXAMPLE 2

Urea-analogs ($R1=CH_2C_6H_5$, $R2=CO—NH—C_6H_5$; boc=tert.-butyloxycarbonyl)

sulfate and then evaporated in vacuum. 4.9 g tert.-butyl 4-(benzylamino)piperidine-1-carboxylate were obtained as oily product.

$^1$H NMR (δ ppm, 400 MHz): 3.82 [s, 2H], 4.01 [2H], 2.81 [2H], 2.67 [1H], 1.86 [2H], 1.30 [2H], 1.45 [s, 9H].

2.2 To a solution of 0.187 ml phenylisocyanate in 25 ml dichloromethane was added dropwise under ice cooling a solution of 0.5 g tert.-butyl 4-(benzylamino)piperidine-1-carboxylate in 20 ml dichloromethane. After 5 hrs. stirring at room temperature the reaction mixture was washed 3 times with water and with a saturated solution of NaCl in water. The organic layer was separated, dried over sodiumsulfate and evaporated in vacuum. The crude product was crystallized from ethylacetate/n-hexane in the refrigerator, yielding 0.55 g tert.-butyl-4-[(anilinocarbonyl)(benzyl)amino]piperidine-1-carboxylate.

$^1$H NMR (δ ppm, 400 MHz): 4.61 [1H], 4.46 [s, 2H], 4.21 [2H], 2.83 [2H], 2.67 [1H], 1.83 [2H], 1.56 [2H], 1.44 [s, 9H].

2.3 Under ice-cooling was added 0.94 ml trifluoroacetic acid to a solution of 0.5 g tert.-butyl-4-[(anilino-carbonyl)(benzyl)amino]piperidine-1-carboxylate in 50 ml dichloromethane. After stirring for 16 hrs. at room temperature the reaction mixture was evaporated under reduced pres-

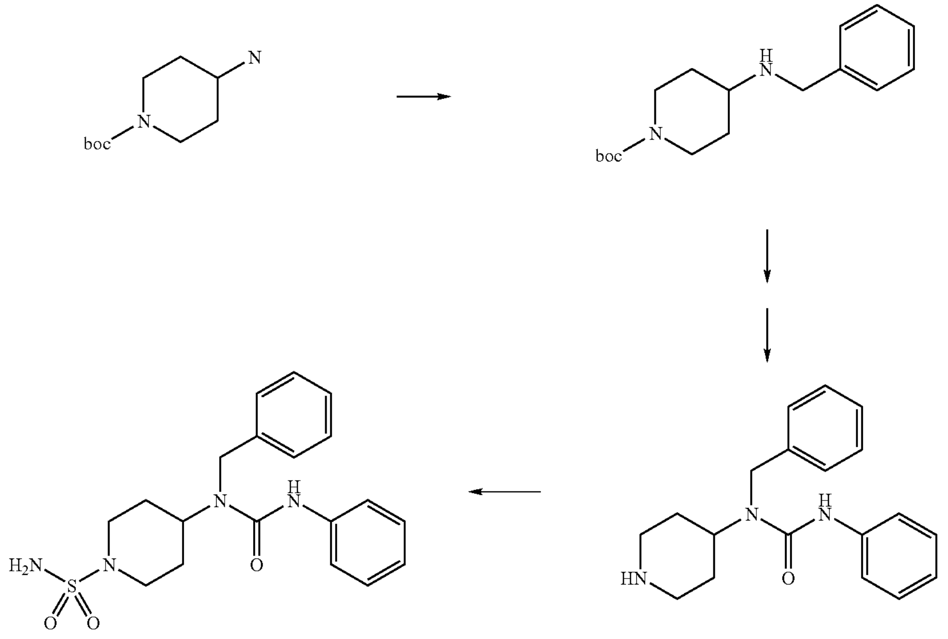

2.1 2.6 g sodium acetate, 5.0 g tert.-butyl-4-aminopiperidine-1-carboxylate, 2.0 ml acetic acid and 2.1 ml benzaldehyde were combined in 200 ml THF and stirred for 4 hrs. at room temperature. After addition of 8.8 g trisacetoxy sodiumborohydride the mixture was stirred for 20 hrs. Then solvent was removed under reduced pressure and the residue was dissolved in a mixture of methyl-tert.-butylether and water. The aqueous layer was made alkaline with NaOH and extracted twice with methyl-tert.-butylether. The combined organic layers were washed three times with 30 ml 0.1N HCl and 5 times with 50 ml 0.1N HCl. Then the aqueous layers were combined and made basic with NaOH, followed by two extractions with methyl-tert.-butylether. The organic layers were washed with water and a saturated solution of NaCl in water, dried over sodium sure and the residue was taken up in a mixture of methyl-tert.-butylether and water. The aqueous layer was made basic by addition of NaOH solution and extracted 3 times with methyl-tert.-butylether. The combined methyl-tert.-butylether layers were washed with a saturated solution of NaCl in water, dried over sodium sulfate and then evaporated in vacuum, yielding 0.23 g of 1-benzyl-3-phenyl-1-piperidin-4yl-urea.

$^1$H NMR (δ ppm, 400 MHz): 4.52 [1H], 4.52 [s, 2H], 3.13 [2H], 2.75 [2H], 1.84 [2H], 1.59 [2H].

2.4 0.2 g of 1-benzyl-3-phenyl-1-piperidin-4yl-urea and 0.075 g sulfamide were dissolved in 50 ml dioxane and refluxed for 5 hrs. The reaction mixture was then concentrated in vacuum and the residue dissolved in water. After stirring for 3 hours the residue was separated by filtration and stirred with methyl-tert.butylether. Filtration and drying in vacuum yielded 0.23 g of crude product, which was purified by flash-chromatography using dichloromethane/methanol (19:1) as eluent. 50 mg of pure 4-[(anilinocarbony)-(benzyl)amino]piperidine-1-sulfonamide were isolated (melting point: 188-189° C.).

EXAMPLE 3

Substituted amides (R1=CH3; R2=$C_6H11$; boc=tert.-butyloxycarbonyl)

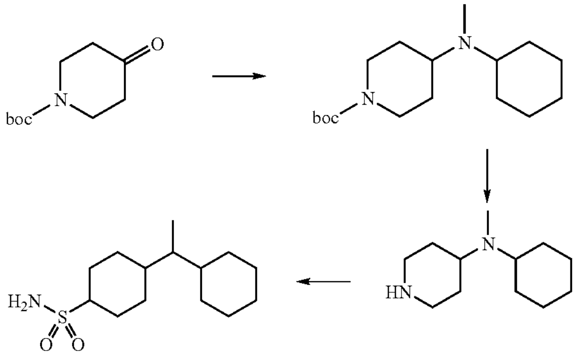

3.1 2.0 g tert.-butyl 4-oxopiperidine-1-carboxylate, 1.23 g sodium acetate, 0.98 ml acetic acid and 1.56 ml N-methylcyclohexanamine were dissolved in 100 ml THF and stirred for one hour at room temperature. Then 4.25 g trisacetoxy sodiumborohydride were added and the reaction mixture was stirred for 18 hours at room temperature. The reaction mixture was concentrated under reduced pressure and the residue was taken up in a mixture of water and methyl-tert.-butylether. The aqueous layer was made alkaline and extracted twice with methyl-tert.-butylether. Finally, the organic layer was washed 2 times with 0.1N HCl, the aqueous layers were combined and made alkaline (pH 10) by addition of NaOH solution. After extraction (2 times) with methyl-tert.-butylether the organic layer was dried over sodium sulfate and evaporated in vacuum. 1.3 g of oily tert-butyl 4-[cyclohexyl-(methyl)amino]piperidine-1-carboxylate were isolated and used without further purification.

$^1$H NMR (δ ppm, 400 MHz): 4.12 [2H], 2.69 [2H], 2.63 [1H], 2.50 [1H], 2.23 [s, 3H], 1.45 [s, 9H].

3.2 1.25 g of tert-butyl 4-[cyclohexyl(methyl)amino]piperidine-1-carboxylate were dissolved in 100 ml dichloromethane, treated with 3.0 ml trifluoroacetic acid and kept for 2 days at room temperature. Then the reaction mixture was concentrated under reduced pressure and the residue was taken up in a mixture of water and methyl-tert.-butylether. The aqueous layer was saturated with sodium chloride and extracted 3 times with methyl-tert.-butylether. The organic layer was dried over sodium sulfate and the solvent removed in vacuum, yielding 0.8 g N-cyclohexyl-N-methylpiperidin-4-amine, which was used without further purification.

$^1$H NMR (δ ppm, 400 MHz): 3.12 [2H], 2.60 [1H], 2.59 [2H], 2.53 [1H], 2.26 [s, 3H].

3.3 0.8 g N-cyclohexyl-N-methylpiperidin-4-amine and 0.47 g sulfamide were dissolved in 70 ml dioxane and refluxed for 3 hours. Then the reaction mixture was concentrated under reduced pressure and the residue was taken up in a mixture of water and methyl-tert.-butylether. The organic layer was washed with water and with a saturated soluteion of NaCl in water, dried over sodium sulfate and then evaporated in vacuum, yielding 0.7 g of 4-[cyclohexyl(methyl)amino]piperidine-1-sulfonamide.

$^1$H NMR (δ ppm, 400 MHz): 6.66 [s, 2H], 3.44 [2H], 2.52 [2H], 2.48 [1H], 2.48 [1H], 2.15 [s, 3H].

The hydrochloride acid salt was formed by treating the amine with HCl in isopropanol and subsequent evaporation of the solvent. The melting point was determined to be 240-242° C.

$^1$H NMR (δ ppm, 400 MHz): 6.86 [2H], 3.34 [2H], 3.32 [s, 3H].

EXAMPLE 4

Substituted amides (R1=H; R2=$C_6H_{11}$; boc=tert.-butyloxycarbonyl)

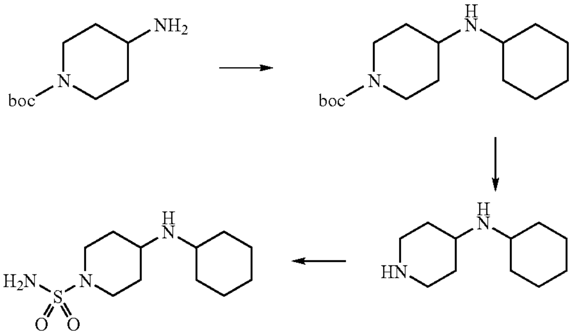

4.1 1.23 g sodium acetate, 2.4 g tert.-butyl-4-aminopiperidine-1-carboxylate, 1.0 ml acetic acid and 1.0 g cyclohexanone were combined in 150 ml THF and stirred for 3 hrs. at room temperature. Then 4.25 g trisacetoxy sodiumborohydride were added and the reaction mixture was stirred for 16 hrs. at room temperature. After concentrating the reaction mixture under reduced pressure the residue was taken up in a mixture of methyl-tert.-butylether and water, which was made alkaline with sodium carbonate to pH 9. The organic layer washed 4 times with 0,1N HCl. Then the aqueous layer was made alkaline with NaOH and extracted twice with methyl-tert.-butylether. The combined organic layers were washed with water and with a saturated solution of NaCl in water, dried over sodium sulfate and then evaporated under reduced pressure, yielding 2.4 g of oily tert-butyl 4-(cyclohexylamino)piperidine-1-carboxylate.

$^1$H NMR (δ ppm, 400 MHz): 4.03 [2H], 2.78 [2H], 2.74 [1H], 2.56 [1H], 1.83 [4H], 1.73 [2H], 1.45 [9H].

4.2 2.3 g of tert-butyl 4-(cyclohexylamino)piperidine-1-carboxylate were dissolved in 100 ml dichloromethane and treated with 6.3 ml trifluoroacetic acid under ice-cooling. After stirring for 16 hrs. at room temperature the reaction mixture was concentrated under reduced pressure. The residue was taken up in a mixture of water and methyl-tert.-butylether. The aqueous layer was made basic with sodium hydroxide and extracted 5 times with methyl-tert.-butylether. Then, the organic layer was washed with water and with a saturated solution of NaCl in water, dried over sodium sulfate and the solvent was removed in vacuum. 1.15 g of oily N-cyclohexyl-piperidin-4-amine were isolated and used without further purification.

$^1$H NMR (δ ppm, 400 MHz): 3.08 [2H], 2.68 [1H], 2.60 [2H], 2.58 [1H], 1.85 [4H], 1.72 [2H].

4.3 1.1 g N-cyclohexyl-piperidin-4-amine and 0.7 g sulfamide were dissolved in 100 ml dioxane and refluxed for 5 hours. Then the solvent was removed under reduced pressure and the remaining residue was taken up in a mixture of water and dichloromethane. The organic layer was washed with water and with a saturated solution of NaCl in water, dried over sodium sulfate and then evaporated in vacuum, yielding 0.8 g 4-(cyclohexylamino)piperidine-1-sulfonamide.

$^1$H NMR (δ ppm, 400 MHz): 6.83 [2H], 3.36 [2H], 2.59 [1H], 2.57 [2H], 2.48 [1H], 1.79 [4H].

The hydrochloride acid salt was formed by treating the amine with HCl in isopropanol and subsequent evaporation of the solvent. The melting point was determined to be higher than 240° C.

$^1$H NMR (δ ppm, 400 MHz): 6.83 [2H], 3.53 [2H], 3.25 [1H], 3.08 [1H], 2.56 [2H], 2.10 [2H].

EXAMPLE 5

Sulfonamides (R1=$CH_2C_6H_5$; R2=$SO_2C_6H_4CH_3$; boc=tert.-butyloxycarbonyl)

g benzylbromide in 5 ml DMF were added dropwise. This mixture was stirred at room temperature for 20 hours. For workup, the solvent was removed under reduced pressure and the residue was taken up in methyl-tert.-butylether. This solution was washed with water and with a saturated solution of NaCl in water, dried over sodium sulfate and finally concentrated in vacuum. The crude product was purified by flash chromatography, using a mixture of n-hexane and ethylacetate (9:1) as eluent. Besides the recovery of 0.69 g starting material 0.51 g tert-butyl 4-{benzyl[(4-methylphenyl)sulfonyl]amino}piperidine-1-carboxylate were isolated.

$^1$H NMR (δ ppm, 400 MHz): 7.76 [2H], 7.41 [2H], 7.38 [2H], 7.33 [2H], 7.25 [1H], 4.39 [s, 2H], 3.86 [1H], 3.80 [2H], 2.63 [2H], 2.41 [s, 3H], 1.31 [s, 9H].

5.3 0.5 g tert-butyl 4-{benzyl[(4-methylphenyl)sulfonyl]amino}piperidine-1-carboxylate and 0.86 ml trifluoroacetic acid were dissolved in 15 ml dichloromethane and stirred for 60 hours at room temperature. The mixture was diluted with dichloromethane and stirred with 0.1N sodium hydroxide solution. Then, the organic layer was separated, was with a saturated solution of NaCl in water,

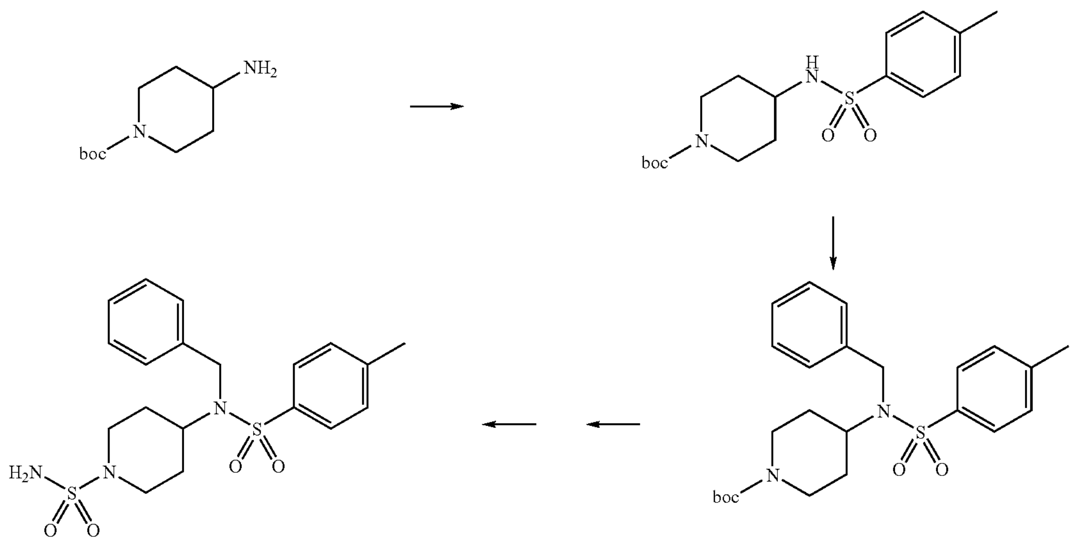

5.1 1.5 g tert.-butyl-4-aminopiperidine-1-carboxylate and 1.13 ml triethylamine were dissolved in 20 ml dichloromethane. To this mixture was added under an atmosphere of nitrogen a solution of 1.57 g p-toluenesulfonylchloride in 15 ml dichloromethane under ice cooling. The reaction mixture was then stirred for 2 days at room temperature. After washing with water, sodium hydrogencarbonate solution, water and with a saturated solution of NaCl in water the organic layer was dried over sodium sulfate and evaporated in vacuum to yield after drying in vacuum 2.6 g tert-butyl 4-{[(4-methylphenyl)sulfonyl]amino}piperidine-1-carboxylate.

$^1$H NMR (δ ppm, 400 MHz): 7.70 [2H], 7.67 [d, 1H], 7.39 [2H], 3.70 [2H], 3.13 [1H], 2.75 [1H], 2.39 [s, 3H], 1.36 [s, 9H].

5.2 To a solution of 1.3 g tert-butyl 4-{[(4-methylphenyl)sulfonyl]amino}piperidine-1-carboxylate in 40 ml DMF were added under cooling with ice and an atmosphere of nitrogen 0.62 g potassium tert.-butylate. After 30 min. 0.69 dried over sodium sulfate and evaporated in vacuum, yielding 0.36 g N-benzyl-4-methyl-N-piperidin-4-ylbenzenesulfonamide.

$^1$H NMR (δ ppm, 400 MHz): 7.74 [2H], 7.40 [2H], 7.39 [2H], 7.34 [2H], 7.25 [1H], 4.40 [s, 2H], 3.69 [1H], 2.77 [21], 2.40 [s, 3H], 2.31 [2H].

5.4 0.36 g N-benzyl-4-methyl-N-piperidin-4-ylbenzenesulfonamide and 0.12 g sulfamide were refluxed in 5 ml dioxane for 8 hours. The reaction mixture was concentrated in vacuum and the residue was taken up in methyl-tert.-butylether, then washed with water, sodium carbonate solution, water and with a saturated solution of NaCl in water. After drying over sodium sulfate the organic layer was evaporated in vacuum to yield 0.4 g 4-{enzyl[(4-methylphenyl)sulfonyl]amino}piperidine-1-sulfonamide.

$^1H$ NMR (δ ppm, 400 MHz): 7.78 [2H], 7.41 [2H], 7.40 [2H], 7.35 [2H], 7.27 [1H], 6.67 [s, 2H], 4.42 [s, 2H], 3.70 [1H], 3.35 [2H], 2.43 [2H], 2.41 [s, 3H].

EXAMPLE 6

Sulfonamides (R1 and R2 build up a phenyl-substituted piperazine-system; boc=tert.-butyloxycarbonyl)

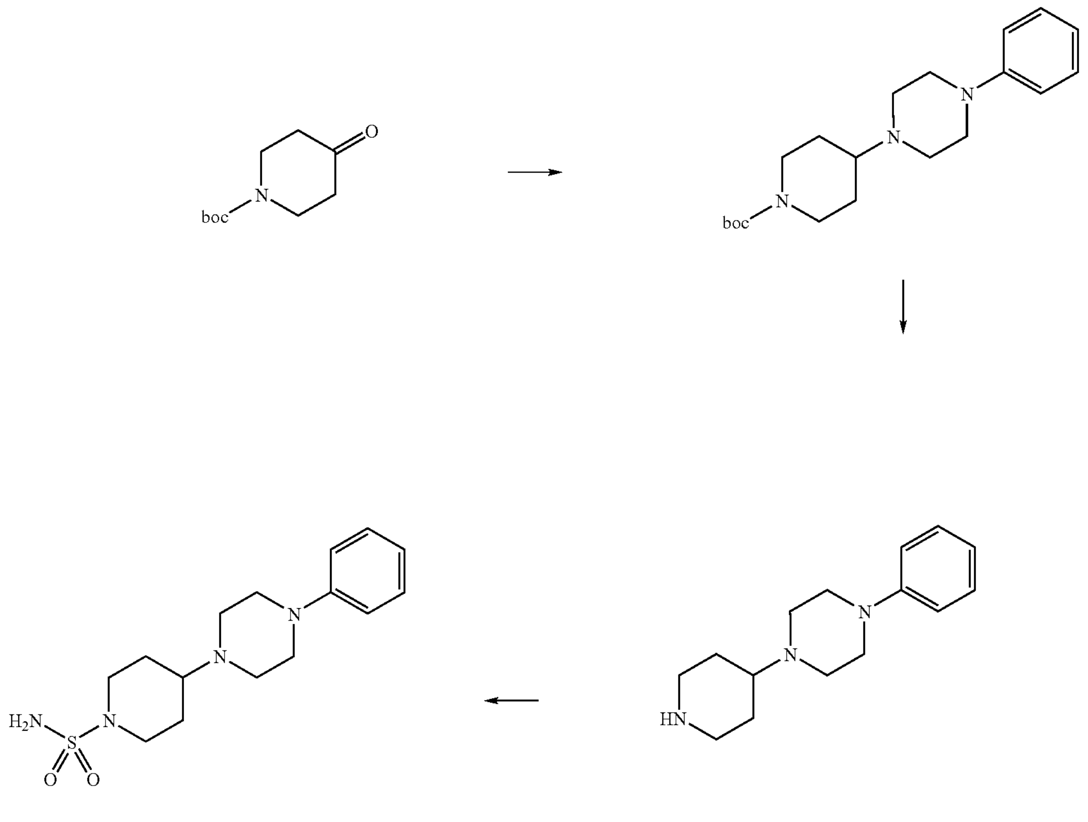

6.1 2.0 g tert-butyl 4-oxopiperidine-1-carboxylate, 1.23 g sodium acetate, 0.98 ml acetic acid and 1.83 ml 1-phenylpiperazine were combined in 150 ml THF and stirred for 2 hours at room temperature. Then, 4.25 g trisacetoxy sodiumborohydride were added and stirred for additional 16 hours. For work-up, the reaction mixture was concentrated in vacuum and the residue was taken up in methyl-tert.-butylether and water. This mixture was made alkaline by addition of a sodium carbonate solution (pH=10). The organic layer was then washed 6 times with 0.1N HCl and the aqueous layer (combined fractions 3, 4 and 5) was made alkaline by the addition of diluted sodium hydroxide solution. After extraction with methyl-tert-butylether, the organic layer was washed with water and with a saturated solution of NaCl in water, dried over sodium sulfate and then concentrated in vacuum. 2.0 g tert-butyl 4-(4-phenylpiperazin-1-yl)piperidine-1-carboxylate were isolated.

$^1H$ NMR (δ ppm, 400 MHz): 7.26 [2H], 6.93 [2H], 6.85 [1H], 4.15 [2H], 3.20 [2H], 2.73 [2H], 2.72 [2H], 2.42 [1H], 1.46 [s, 9H].

6.2 1.9 g tert-butyl 4-(4-phenylpiperazin-1-yl)piperidine-1-carboxylate and 4.25 ml trifluoroacetic acid were dissolved in 100 ml dichloromethane and stirred for 24 hours. The reaction mixture was concentrated in vacuum and the remaining residue was taken up in methyl-tert.-butylether and water. After basification with sodium hydroxide solution the aqueous layer was extracted with methyl-tert-butylether. Then the precipitate in the aqueous layer was isolated by filtration, washed with water and dried in vacuum at 50° C., yielding 0.67 g 1-phenyl-4-piperidin-4-ylpiperazine.

$^1H$ NMR (δ ppm, 400 MHz): 7.25 [2H], 6.93 [2H], 6.85 [1H], 3.21 [2H], 3.16 [2H], 2.73 [2H], 2.61 [2H], 2.38 [1H].

6.3 0.65 g 1-phenyl-4-piperidin-4-ylpiperazine and 0.30 g sulfamide were dissolved in 50 ml dioxane and refluxed for 3 hours. The reaction mixture was concentrated under reduced pressure. When the residue was taken up with water, a precipitation started which was completed by further stirring for 1 hour. After filtration, the precipitate was stirred in the presence of dichloromethane for 1 hour, again filtered and dried in vacuum at 50° C. 0.68 g 4-(4-phenylpiperazin-1-yl)piperidine-1-sulfonamide were isolated.

$^1H$ NMR (δ ppm, 400 MHz): 7.20 [2H], 6.92 [2H], 6.76 [1H], 6.69[s, 2H], 3.50 [2H], 3.11 [2H], 2.64 [2H], 2.54 [2H], 2.31 [1H].

This compound was transferred to the corresponding HCl salt by treatment with a HCl/isopropanol solution. Recrystallization yielded 0.52 g product, melting point 222-227° C.

EXAMPLE 7

Alternative Introduction of the Sulfonamide Function

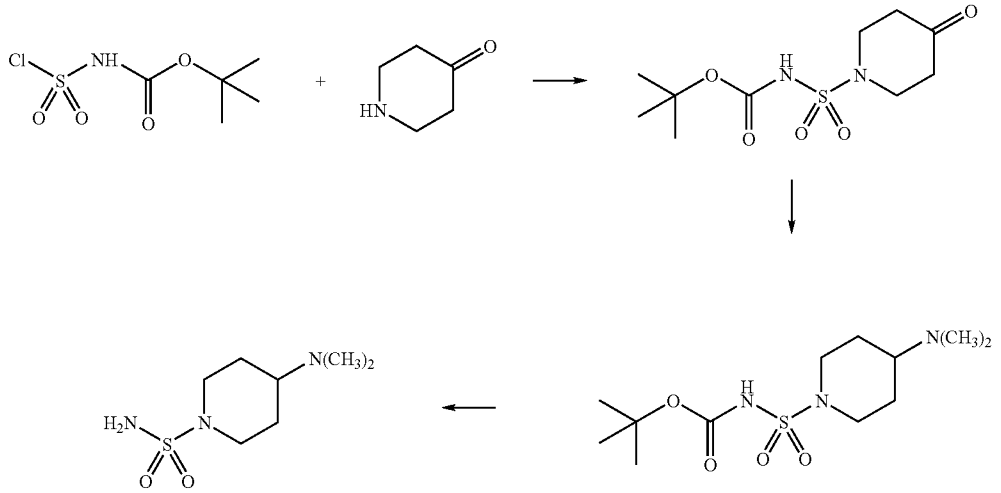

7.1 To an ice-cooled solution of 4.36 ml chlorosulfonyl isocyanate in 50 ml dichloromethane was added dropwise over a period of 30 minutes a solution of 4.8 ml tert.-butanol in 50 ml dichloromethane. After further stirring for 30 minutes under cooling, this mixture was added dropwise to a solution of 7.68 g 4-piperidone hydrate HCl-salt and 14.6 ml triethylamine in 100 ml dichloromethane. After stirring for 45 minutes under cooling the reaction mixture was allowed to come to room temperature and was stirred for 16 hours. The reaction mixture was diluted with dichloromethane, washed 3 times with 0.1N HCl (60 ml each) and with a saturated solution of NaCl in water. After drying over sodium sulfate the organic layer was concentrated in vacuum to yield 7.2 g of crude product. Purification via flash-chromatography, using a mixture of dichloromethane/methanol (9:1) as eluent gave 6.0 g tert-butyl [(4-oxopiperidin-1-yl)sulfonyl]carbamate.

$^1$H NMR (δ ppm, 400 MHz, DMSO-$d_6$): $^1$H-NMR: 3.56 [t, 4H], 2.44 [t, 4H], 1.42 [s, 9H].

Further reaction steps as in any of the above examples 1 to 6.

EXAMPLE 8

Alternative Introduction of the Sulfonamide Function

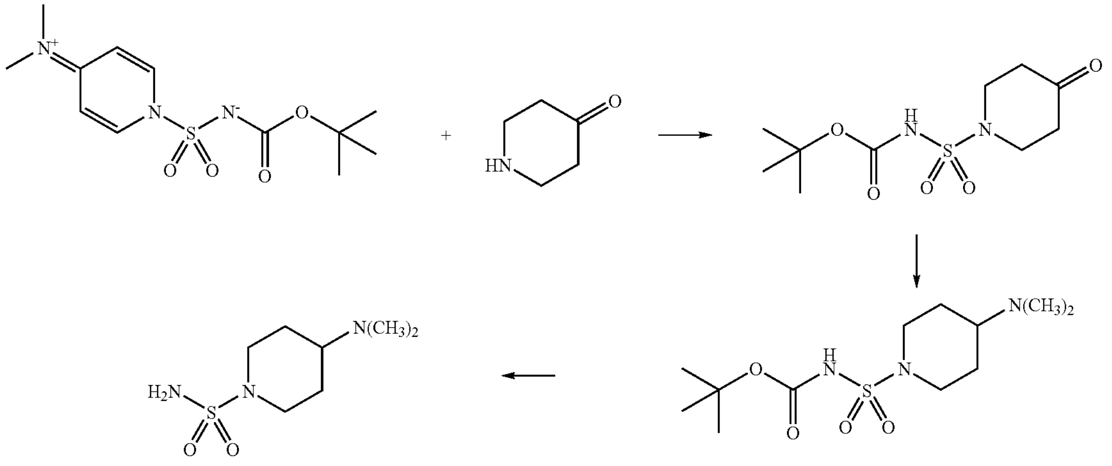

8.1 To a solution of 2.6 ml tert.-butanol in 20 ml dichloromethane were added dropwise under cooling with ice 2.4 ml chlorosulfonyl isocyanate over 15 minutes. After stirring for 15 minutes 6.9 g 4-dimethyl-amino pyridine were added. The cooling was removed and the reaction mixture was stirred for 1 hour at room temperature, when a white precipitate was formed. The mixture was diluted with 130 ml dichloromethane and washed for times with water and finally with a saturated solution of NaCl in water. After drying over sodium sulfate the organic layer was concentrated in vacuum to yield 6.4 g of the crystalline reagent (tert-butoxycarbonyl){[4-(dimethyliminio)pyridin-1(4H)-yl]sulfonyl}azanide.

$^{1}$H NMR (δ ppm, 400 MHz, $CDCl_3$): 8.46 [d, 2H], 6.98 [d, 2H], 3.23 [s, 6H], 1.26 [s, 9H].

8.2 0.5 g (tert-butoxycarbonyl){[4-(dimethyliminio)pyridin-1(4H)-yl]sulfonyl}azanide, 0.26 g 4-piperidone hydrate HCl-salt and 0.205 g 4-dimethylamino pyridine were dissolved in 50 ml dioxane and heated at 50° C. for 4 hours. The reaction mixture was concentrated in vacuum and the residue was taken up in dichloromethane. After washing twice with diluted potassium hydrogensulfate solution, the organic layer was washed with a saturated solution of NaCl in water and dried over sodium sulfate. The solvent was removed under reduced pressure, yielding 0.23 tert-butyl [(4-oxopiperidin-1-yl)sulfonyl]-carbamate. A further amount of 0.07 g of product was obtained by extracting the combined aqueous layers with dichloromethane.

$^{1}$H NMR (δ ppm, 400 MHz, $CDCl_3$): 3.74 [t, 4H], 2.58 [t, 4H], 1.49 [s, 9H].

Further reaction steps as in any of the above examples 1 to 6.

EXAMPLE 9

Substituted sulfonamides

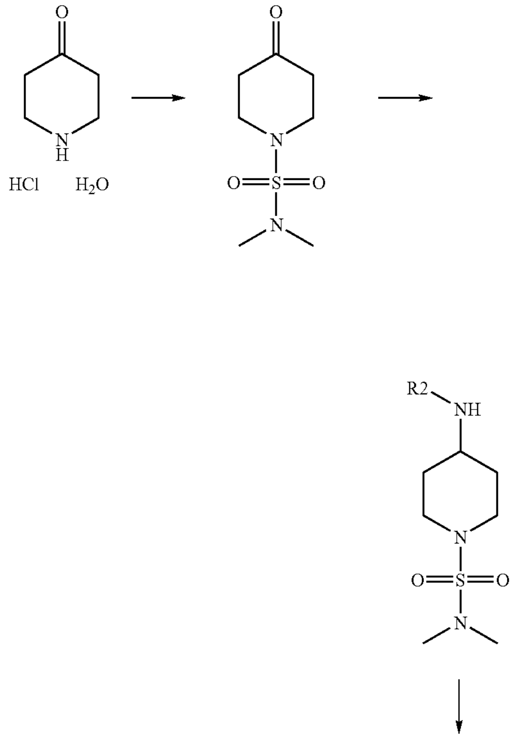

-continued

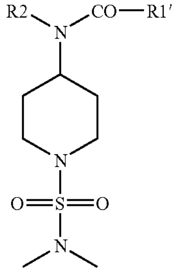

9.1 10 g (65 mmol) piperidone hydrochloride and 7.7 ml (1.1 eq, 71.6 mmol) dimethyl sulfamoyl chloride were dissolved in a mixture of acetone/water (1:1, 400 ml). 20 ml (2.2 eq, 143 mmol) triethylamine was added and the reaction was stirred at room temperature for 4 days. The solvent was then evaporated and the residue dissolved in ethyl acetate. The organic layer was then washed with water, dried over magnesium sulfate, and the solvent removed in vacuum, to give the required sulfamide as a white solid (12.55 g, 95% yield).

$^{1}$H NMR (δ ppm, 400 MHz, $CDCl_3$): 2.49 (t, 4H, J=6.24 Hz), 2.79 (s, 6H), 3.53 (t, 4H, J=6.12 Hz).

9.2 0.35 g (1.7 mmol) of the sulfamide from step 9.1 was dissolved in 10 ml dichloroethan, followed by 1.05 eq (1.78 mmol) of pentylamine and 1.5 eq (2.55 mmol) trisacetoxy sodiumborohydride. The reaction was stirred at room temperature overnight and was then washed with 1M NaOH. The aqueous layer was extracted with ether. The combined organic layers were washed with a saturated solution of NaCl in water, then dried over magnesium sulfate, and the solvent removed in vacuum. The crude was loaded onto 0.5 g polymer-supported toluenesulfonic acid. The resin was washed with MeOH, then with 2M $N_3$ in MeOH to recover pure amine.

$^{1}$H NMR (δ ppm, 400 MHz, $CDCl_3$): 0.69 (t, 3H, J=7 Hz), 1.20 (m, 9H), 1.72 (m, 2H), 2.38 (m, 1H), 2.42 (t, 2H, J=7 Hz), 2.60 (s, 6H), 2.65 (td, 2H, J=2, 13 Hz), 3.43 (2H, td, J=3, 13 Hz).

$^{13}$C NMR (δ ppm, 400 MHz, $CDCl_3$): 14.0, 22.6, 29.6, 30.1, 32.3, 38.2, 45.2, 46.9, 54.3.

9.3 0.036 mmol of the amine from step 9.2 was dissolved in 1 ml dichloromethane and mixed with 1.5 eq, 0.054 mmol acetic acid chloride and 0.054 mmol (1.5 eq, 15 mg) polymer-supported triethylamine. The reaction was shaken for 3 days at room temperature, before 0.054 mmol (1.5 eq, 26 mg) aminomethylated polystyrene was added to the reaction mixture. It was then shaken for 1 more day. The resin was filtered off, rinsed with dichloroethane and the solvent was evaporated in vacuum to recover the desired sulfamamides.

EXAMPLE 10

Substituted Sulfonamides (boc=tert.-butyloxycarbonyl)

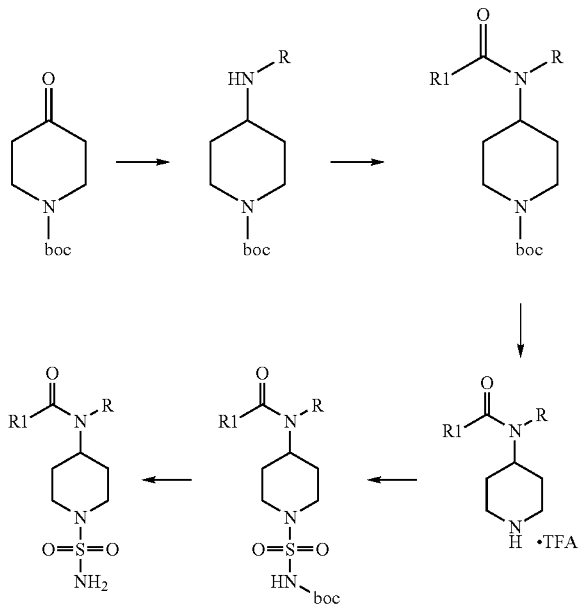

10.1 0.35 g (17.57 mmol) tert-butyl 4-oxopiperidine-1-carboxylate were dissolved in 100 ml dichloroethane, followed by the addition of 1.05 eq (18.44 mmol) of the amine and 1.5 eq. (26.36 mmol) of trisacetoxy sodiumborohydride. The reaction was stirred at room temperature overnight. The reaction mixture was then washed with 1M NaOH, and the aqueous layer was extracted with ether. The combined organic layer was washed with a saturated solution of NaCl in water, then dried over magnesium sulfate, and the solvent was removed in vacuum to get the required pure amine substituted piperidine.

10.2 18 mmol of the amine substituted piperidine from step 10.1 were dissolved in 120 ml dichloromethane and mixed with 19.8 mmol (1.1 eq.) of the acid chloride and 27 mmol (3.76 ml, 1.5 eq.) of triethylamine. The reaction was stirred for 3 days at room temperature. The reaction mixture was then quenched with a saturated solution of NaCl in water, and the aqueous layer was extracted with dichloromethane. The combined organic layer was dried over magnesium sulfate, and the solvent evaporated in vacuum. The crude compound was purified by flash chromatography eluting with 40-50% ethyl acetate/heptane, to give the desired carbonyl substituted piperidine.

10.3 12.21 mmol of the carbonyl substituted piperidine from step 10.2 were dissolved in 20% trifluoroacetic acid in 45 ml dichloromethane. The reaction was stirred for 1 h. The solvent was evaporated in vacuum to get the desired carbonyl substituted piperidine as a trifluoroacetic acid salt in quantitative yield. The compound was not purified further and was used crude in the next step.

10.4 0.84 mmol of carbonyl substituted piperidine as a trifluoroacetic acid salt from step 10.3 were dissolved in 20 ml dichloroethane, and 9.51 mmol (3 g) tetraalkylammonium carbonate, polymer-bound was added to the mixture. The reaction was stirred for 1 day before the resin was filtered and rinsed with dichloromethane. The solvent was removed to get the carbonyl substituted piperidine as a free base amine.

1.68 mmol (2 eq.) tert-butanol was added slowly to a solution of 1.68 mmol (2 eq., 0.145 ml) chlorosulfonylisocyanate 10 ml dichloromethane at 0° C. The reaction was warmed to room temperature for 1 h, before it was cooled down to 0° C. 0.47 ml (3.36 mmol; 4 eq.) triethylamine was added to the reaction followed by the free based amine from step 10.4 above in 5 ml dichloromethane. The reaction was warmed to room temperature and stirred over night. The reaction mixture was washed with 1N HCl, the organic layer was dried over magnesium sulfate, and the solvent evaporated in vacuum. The crude compound was purified by flash chromatography, eluting with 50% ethyl acetate/heptane, to get the boc-protected sulfamamide as a white solid (0.185 g, 55% yield).

10.5 0.12 mmol of the boc-protected sulfamide from step 10.4 were dissolved in 20% TFA in 1 ml dichloromethane and the reaction was stirred for 2 h. The solvent was then evaporated in vacuum to get a white solid, the desired end product as trifluoroacetic acid salt in quantitative yield (42 mg).

EXAMPLE 11

Heteroaryl-Substituted Sulfonamides (boc=tert.-butyloxycarbonyl)

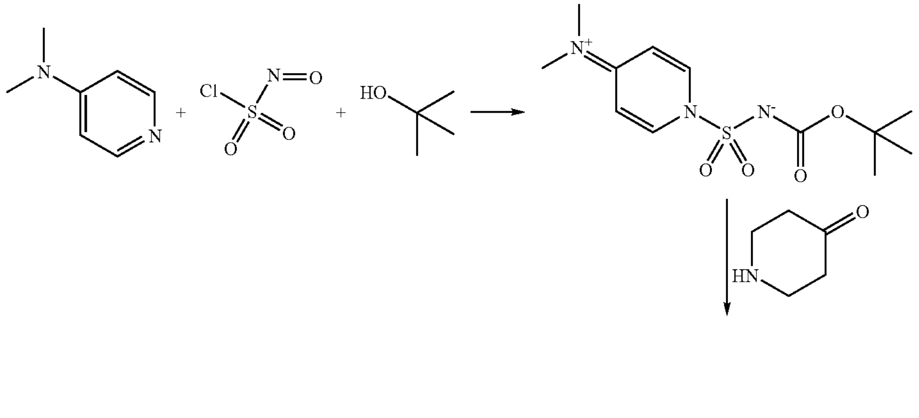

-continued

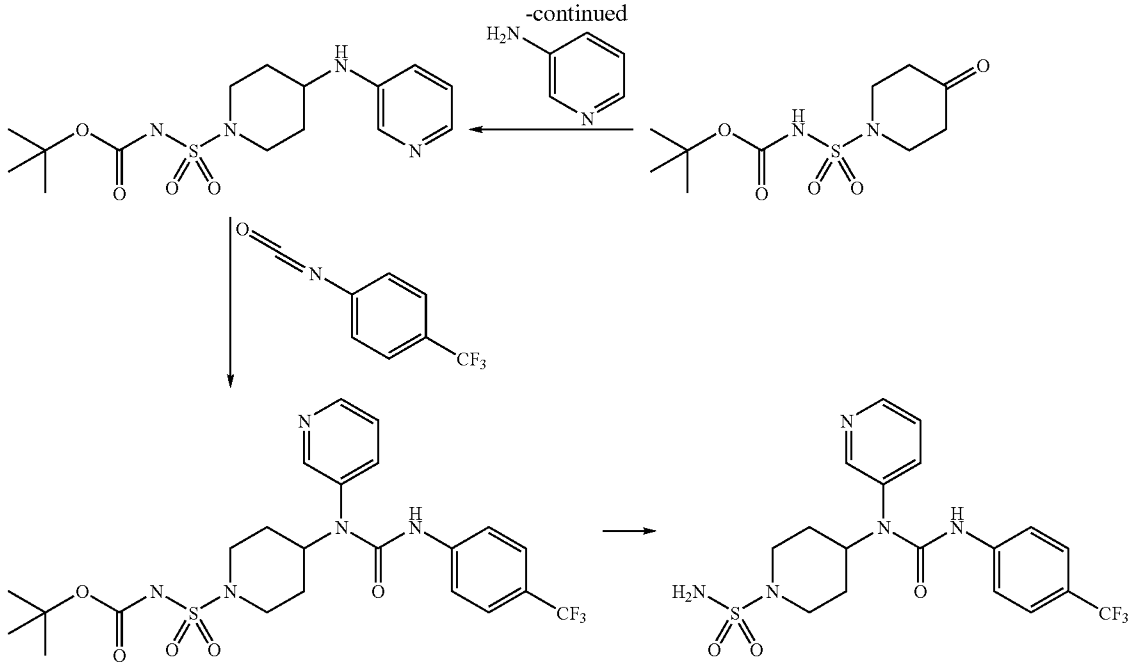

11.1 To a solution of 26 mL tert.-butanol in 200 mL dichloromethane were added dropwise under cooling with ice (5° C.) 24 mL chlorosulfonyl isocyanate over 90 minutes. After stirring for 60 minutes, 69 g 4-dimethylamino pyridine were added in portions. The cooling was removed and the reaction mixture was stirred for 1 hour at room temperature, when a white precipitate was formed. The mixture was diluted with 200 mL dichloromethane and washed with 500 mL water. Then 1.1 L dichloromethane was added and the resulting solution was washed four times with water (0.5 L each) and finally with brine. After drying over sodium sulfate the organic layer was concentrated in vacuum to yield 76.5 g of the crystalline reagent (tert-butoxycarbonyl){[4-(dimethyliminio)pyridin-1(4H)-yl] sulfonyl}azanide with a melting point of 180-181° C.

1H-NMR (δ ppm, 400 MHz, $CDCl_3$): 8.46 [d, 2], 6.98 [d, 2], 3.23 [s, 6], 1.26 [s, 9]

11.2 50 g (tert-butoxycarbonyl){[4-(dimethyliminio)pyridin-1(4H)-yl]sulfonyl}azanide, 30.6 g 4-piperidone hydrate HCl-salt and 24.3 g 4-dimethylamino pyridine were dissolved in 1.5 L dioxane and heated at 55° C. for 16 hours. The reaction mixture was concentrated in vacuum and the residue was taken up in dichloromethane. After washing three times with diluted potassium hydrogensulfate solution, the organic layer was washed with brine and dried over sodium sulfate. The solvent was removed under reduced pressure, yielding 32.8 g tert-butyl [(4-oxopiperidin-1-yl)sulfonyl]-carbamate with a melting point of 107-109° C.

$^1$H NMR (δ ppm, 400 MHz, $CDCl_3$): 3.74 [t, 4], 2.58 [t, 4], 1.49 [s, 9]

11.3 14 g tert-butyl [(4-oxopiperidin-1-yl)sulfonyl]carbamate were dissolved in 600 mL THF and 5.7 g 3-aminopyridine and 6.2 g sodium acetate were added. To this mixture were added 4.9 mL acetic acid and 7.4 mL tetraisopropyl orthotitanate and then the reaction mixture was stirred for 5 hours at room temperature. Then, 21.3 g sodium trisacetoxyborohydride were added in portions and it was stirred for 16 hours at room temperature. The reaction mixture was concentrated in vacuum and the residue was taken up in a mixture of dichloromethane and water. The aqueous layer and some solid was separated and stirred with dichloromethane. For a better separation the combined organic layers were treated in a centrifuge (4000 rpm). The organic layer was washed with brine and dried over sodium sulfate, to yield after evaporation under reduced pressure 20 g of a light green oil. Crystalization from MTB-E (100 mL) gave 8.34 g of pure tert-butyl {[4-(pyridin-3-ylamino)piperidin-1-yl]sulfonyl}carbamate having a melting point of 170° C. (dec.).

$^1$H NMR (δ ppm, 400 MHz, DMSO-$d_6$): 10.92 [s, br, 1], 8.00 [d, 1], 7.76 [dd, 1], 7.11 [dd, 1], 7.02 [dd, 1], 3.62 [m, 2], 3.42 [m, 1], 2.99 [m, 2], 1.97 [m, 2], 1.44 [s, 9], 1.38 [m, 2].

11.4 28.6 g tert-butyl {[4-(pyridin-3-ylamino)piperidin-1-yl] sulfonyl}carbamate were nearly complete dissolved in 1.5 L dichloromethane and then 15 g 4-(trifluoromethyl)-phenyl isocyanate were added. This reaction mixture was stirred for 24 h at 40° C. The reaction mixture was filtered (0.9 g starting material was isolated) and concentrated in vacuum. The residue was stirred in a mixture of 500 mL of MTB-E and 500 mL of water for 1 hour, when the product started to precipitate. The solid was separated by filtration, washed with MTB-E and water and then dried in vacuum at 60° C. 41.4 g tert-butyl {[4-(pyridin-3-yl{[4-(trifluoromethyl)phenyl]-carbamoyl}amino)-piperidin-1-yl] sulfonyl}carbamate were isolated having a melting point of 145° C. (foaming).

$^1$H NMR (δ ppm, 400 MHz, DMSO-$d_6$): 10.88 [s, br, 1], 8.61 [d, 1], 8.45 [dd, 1], 8.11 [s, 1], 7.70 [dd, 1], 7.61 [d, 2], 7.55 [d, 2], 7.50 [dd, 1], 4.43 [m, 2], 3.67 [m, 1], 2.95 [m, 2], 1.92 [m, 2], 1.36 [s, 9], 1.22 [m, 2].

11.5 To a solution of 1.3 g tert-butyl {[4-(pyridin-3-yl{[4-(trifluoromethyl)phenyl]-carbamoyl}amino)-piperidin-1-yl]sulfonyl}carbamate in 100 mL dichloromethane were added 1.8 mL trifluoroacetic acid. This mixture was stirred for 30 hours at room temperature. Then the reaction mixture was concentrated in vacuum and the resulting oily residue was taken up in MTB-E, where the product begun to crystallize. After 2 hours the solid was isolated by filtration and thereafter dried under reduced pressure. The resulting residue was stirred with a mixture of MTB-E and water. After removal of some insoluble product (0.13 g) the organic layer was separated, washed with water and sodium hydrogencarbonate solution, when the product precipitated. The yield of the combined crystalline material 4-(pyridin-3-yl{[4-(trifluoromethyl)phenyl]carbamoyl}-amino)piperidine-1-sulfonamide was 0.57 g having a melting point of 188-191° C.

$^1H$ NMR (δ ppm, 400 MHz, DMSO-$d_6$): 8.62 [d, 1], 8.47 [dd, 1], 8.14 [s, 1], 7.71 [dd, 1], 7.62 [d, 2], 7.55 [d, 2], 7.52 [dd, 1], 4.36 [m, 2], 3.50 [m, 1], 2.62 [m, 2], 1.93 [m, 2], 1.26 [m, 2].

The compounds listed in the following Table 3 have been synthesized in excellent yields in accordance with the procedures described in the foregoing Examples 1 through 8.

TABLE 3

Further compounds of Formula I

| Compound No. | Example No. | R1 | R2 | R3 | R4 |
|---|---|---|---|---|---|
| 1 | 1 | H | CO—NH—$C_6H_4F$ | H | H |
| 2 | 2 | $CH_2C_6H_5$ | CO—NH—$C_6H_5$ | H | H |
| 3 | 3 | $CH_3$ | $C_6H_{11}$ | H | H |
| 4 | 4 | H | $C_6H_{11}$ | H | H |
| 5 | 5 | $CH_2C_6H_5$ | $SO_2C_6H_4CH_3$ | H | H |
| 6 | 6 | | 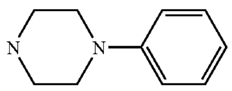 | H | H |
| 7 | 7 | $CH_3$ | $CH_3$ | H | H |
| 8 | 8 | $CH_3$ | $CH_3$ | H | H |
| 9 | 1 | | 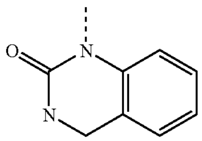 | H | H |
| 10 | 1 | | 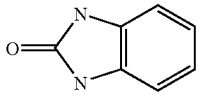 | H | H |
| 11 | 1 | | 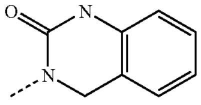 | H | H |
| 12 | 2 | H | CO—$C_6H_4$-4-$OCH_3$ | H | H |
| 13 | 2 | H | CO-tert-$C_4H_9$ | H | H |
| 14 | 3 | $CH_3$ | $C_6H_5$ | H | H |
| 15 | 3 | $CH_3$ | $C_6H_{11}$ | H | H |
| 16 | 3 | $C_2H_5$ | $C_6H_{11}$ | H | H |
| 17 | 2 | H | CO—NH—$C_6H_4$-4-F | H | H |
| 18 | 2 | H | CO—NH—$C_6H_4$-4-OH | H | H |
| 19 | 2 | H | $C_6H_5$ | H | H |
| 20 | 2 | H | $C_6H_{11}$ | H | H |
| 21 | 6 | | 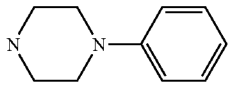 | H | H |
| 22 | 2 | H | CO—NH—$C_6H_4$-3-F | H | H |
| 23 | 2 | H | CO—NH—$C_6H_4$-4-$CF_3$ | H | H |
| 24 | 3 | $CH_3$ | $C_6H_4$-4-$OCH_3$ | H | H |
| 25 | 6 | | 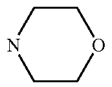 | H | H |
| 26 | 3 | $CH_2C_6H_5$ | CO—NH—$C_6H_{11}$ | H | H |
| 27 | 3 | $CH_2C_6H_5$ | CO—NH—$C_6H_{13}$ | H | H |

TABLE 3-continued

Further compounds of Formula I

| Compound No. | Example No. | R1 | R2 | R3 | R4 |
|---|---|---|---|---|---|
| 28 | 3 | $CH_2C_6H_5$ | CO—NH—$C_6H_5$ | H | H |
| 29 | 3 | $CH_2C_6H_5$ | CO—NH—$CH_2C_6H_5$ | H | H |
| 30 | 2 | H | CO—NH—$C_6H_4$-4-$OCH_3$ | H | H |
| 31 | 2 | H | CO—NH—$CH_2C_6H_4$-4-F | H | H |
| 32 | 3 | $C_6H_{11}$ | CO—NH—$CH_2C_6H_5$ | H | H |
| 33 | 3 | $CH_2C_6H_5$ | CO—NH-3-$C_6H_4N$ | H | H |
| 34 | 2 | H | 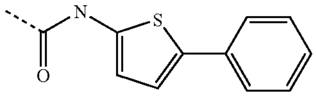 | H | H |
| 35 | 2 | H | CO—NH CO—NH—$C_6H_4$-4-$OCF_3$ | H | H |
| 36 | 3 | $C_6H_{11}$ | CO—NH—$C_6H_5$ | H | H |
| 37 | 6 | | 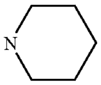 | H | H |
| 38 | 9 | $(CH_2)_2OCH_3$ | $COCH_3$ | $CH_3$ | $CH_3$ |
| 39 | 9 | $(CH_2)_2CH(CH_3)_2$ | $COCH_3$ | $CH_3$ | $CH_3$ |
| 40 | 9 | $(CH_2)_4CH_3$ | $COCH_3$ | $CH_3$ | $CH_3$ |
| 41 | 9 | $CH_2C_6H_{11}$ | $COCH_3$ | $CH_3$ | $CH_3$ |
| 42 | 9 | $CH_2C_6H_5$ | $COCH_3$ | $CH_3$ | $CH_3$ |
| 43 | 9 | $CH_2C_6H_4$-4-$CH_3$ | $COCH_3$ | $CH_3$ | $CH_3$ |
| 44 | 9 | $CH_2C_6H_4$-4-F | $COCH_3$ | $CH_3$ | $CH_3$ |
| 45 | 9 | $CH_2C_6H_4$-4-$OCH_3$ | $COCH_3$ | $CH_3$ | $CH_3$ |
| 46 | 9 | $CH_2C_6H_4$-3-Cl | $COCH_3$ | $CH_3$ | $CH_3$ |
| 47 | 9 | $CH_2C_6H_4$-4-$N(CH_3)_2$ | $COCH_3$ | $CH_3$ | $CH_3$ |
| 48 | 9 | $CH_2$-4-$C_5H_4N$ | $COCH_3$ | $CH_3$ | $CH_3$ |
| 49 | 9 | $CH_2$-3-$C_5H_4N$ | $COCH_3$ | $CH_3$ | $CH_3$ |
| 50 | 10 | $CH_3$ | $COC_6H_5$ | H | H |
| 51 | 10 | $CH_3$ | $CO(CH_2)_2C_6H_5$ | H | H |
| 52 | 10 | $CH_2C_6H_{11}$ | $COC_6H_5$ | H | H |
| 53 | 10 | $CH_2C_6H_{11}$ | $C_2H_5$ | H | H |
| 54 | 10 | $CH_2C_6H_{11}$ | $COC_5H_9$ | H | H |
| 55 | 10 | $CH_2C_6H_{11}$ | $CON_5H_4N$ | H | H |
| 56 | 10 | $CH_2C_6H_4$-4-F | $COC_6H_5$ | H | H |
| 57 | 10 | $CH_2C_6H_4$-4-F | $COC_6H_{11}$ | H | H |
| 58 | 10 | $CH_2C_6H_5$ | $COC_5H_9$ | H | H |
| 59 | 10 | $CH_2C_5H_5N$ | $COC_5H_9$ | H | H |
| 60 | 9 | $CH_3$ | $C_6H_{11}$ | 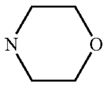 | |
| 61 | 9 | $CH_3$ | $C_6H_{11}$ | H | C3H5 |
| 62 | 9 | $CH_3$ | $C_6H_{11}$ | H | C6H11 |
| 63 | 9 | $CH_3$ | $C_6H_{11}$ | H | CH3 |
| 64 | 9 | $CH_3$ | $C_6H_{11}$ | 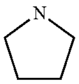 | |
| 65 | 9 | $CH_3$ | $C_6H_{11}$ | 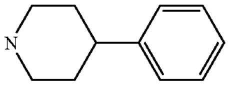 | |
| 66 | 9 | $CH_3$ | $C_6H_{11}$ | CH3 | C6H11 |
| 67 | 9 | $CH_3$ | $C_6H_{11}$ | 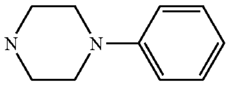 | |
| 68 | 11 | 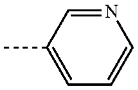 | $CONH(C_6H_4$-4-$CF_3)$ | H | H |

TABLE 3-continued

Further compounds of Formula I

| Compound No. | Example No. | R1 | R2 | R3 | R4 |
|---|---|---|---|---|---|
| 69 | 11 | H | $CON(C_6H_5)_2$ | H | H |
| 70 | 11 | H | $CON(C_2H_5)_2$ | H | H |
| 71 | 11 | H | 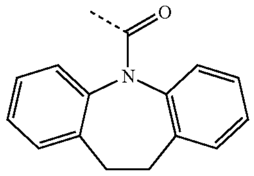 | H | H |
| 72 | 11 | H | 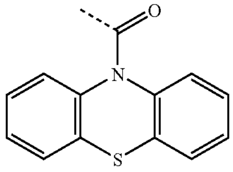 | H | H |
| 73 | 11 | H | 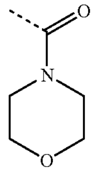 | H | H |
| 74 | 11 | $S(O)_2NH_2$ | 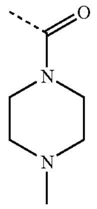 | H | H |

EXAMPLE I

Capsules containing Compound I from example 6

| | |
|---|---|
| Compound I from example 6 | 70 mg |
| Corn starch | 60 mg |
| Lactose | 250 mg |
| Ethylacetate (=EA) | q.s. |

The active substance, the corn starch and the lactose are processed into a homogeneous pasty mixture using EA. The paste is ground and the resulting granules are placed on a suitable tray and dried at 45° C. in order to remove the solvent. The dried granules are passed through a crusher and mixed in a mixer with the further following auxiliaries:

| | |
|---|---|
| Talcum | 5 mg |
| Magnesium stearate | 5 mg |
| Corn starch | 10 mg |

and are then poured into 400 mg capsules (=capsule size 0).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims, and equivalents thereof.

What is claimed is:

1. A compound corresponding to Formula I:

I

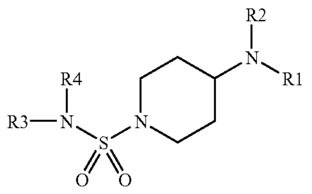

wherein

R1 is selected from the group consisting of H; alkyl; cycloalkyl; alkylenealkoxy; alkylenecycloalkyl; aryl unsubstituted or substituted by one or more alkyl, alkoxy, halogen, $CF_3$, CN; alkylenearyl; alkylenearylenealkyl; alkylenearylenehalogen; alkylenearyleneoxyalkyl; alkylenearylenedialkylamin; heteroaryl; alkyleneheteroaryl unsubstituted or substituted with alkyl, alkoxy, halogen, CN, $CF_3$;

R2 is selected from the group consisting of cycloalkyl; aryl unsubstituted or substituted with alkyl, alkoxy, halogen, CN, $CF_3$; alkylenearyl, unsubstituted or substituted, but not substituted by furan or furanyl; alkylenealkoxy; alkylenecycloalkyl; CO-alkyl; CO-cycloalkyl; CO-aryl substituted by alkyl, alkoxy, halogen, $CF_3$, CN; CO-alkylenearyl unsubstituted or substituted with alkyl, alkoxy, halogen, $CF_3$, CN; CO-heteroaryl unsubstituted or substituted by alkyl, alkoxy, halogen, $CF_3$, CN; CO—O-alkyl; CO—O-cycloalkyl; CO—O-aryl substituted with alkyl, alkoxy, halogen, CN, $CF_3$; CO—O-alkylenearyl unsubstituted or substituted with alkyl, alkoxy, halogen, CN, $CF_3$; CO—O-heteroaryl; CO—NH-alkyl; CO—NH-cycloalkyl; CO—NH-aryl substituted with alkyl, alkoxy, halogen, CN, $CF_3$; CO—NH-alkylenearyl unsubstituted or substituted with alkyl, alkoxy, halogen, CN, $CF_3$; CO—NH-heteroaryl; $SO_2$—$NH_2$; $SO_2$-alkyl; $SO_2$-aryl unsubstituted or substituted by alkyl, alkoxy, halogen, $CF_3$, CN; or R1 and R2 together form a 5 or 6-membered ring which may optionally contain from 1 to 2 additional heteroatoms independently selected from the group consisting of nitrogen, oxygen and sulfur; and which may optionally bear 1 or 2 double bonds; and which may also be substituted by alkyl, halogenalkyl, aryl unsubstituted or substituted with alkyl, alkoxy, hydroxy, halogen, CN, $CF_3$, and/or heteroaryl; and which may also contain a carbonyl group; and which may also be condensed with aryl;

R3 and R4 are each independently selected from the group consisting of H, cycloalkyl, cycloalkyl containing 1 or more heteroatoms selected from nitrogen and oxygen; cycloalkyl containing 1 or more heteroatoms selected from nitrogen and oxygen, and optionally substituted with alkyl, alkoxy, halogen, $CF_3$, CN; aryl; aryl substituted with alkyl, alkoxy, halogen, $CF_3$, CN; and heteroaryl unsubstiututed or substituted with alkyl, alkoxy, halogen, $CF_3$, CN; or R3 and R4 together form a 5 or 6-membered ring which may optionally contain from 1 to 2 heteroatoms independently selected from the group consisting of nitrogen and oxygen atoms and which may also be substituted by aryl or aryl substituted with alkyl, alkoxy, halogen, $CF_3$ and CN;

or a physiologically acceptable acid addition salt thereof.

2. A compound according to claim 1, wherein:

R1 is selected from the group consisting of H; alkyl; cycloalkyl; alkylenealkoxy; alkylenecycloalkyl; aryl; alkylenearyl; heteroaryl; alkyleneheteroaryl unsubstituted or substituted with halogen;

R2 is selected from the group consisting of cycloalkyl; aryl substituted with alkyl, alkoxy, halogen, CN, $CF_3$; alkylenearyl, unsubstituted or substituted, but not substituted by furan or furanyl; alkylenealkoxy; alkylenecycloalkyl; CO-alkyl; CO-cycloalkyl; CO-alkylenearyl; CO-heteroaryl; CO—O-alkyl; CO—O-cycloalkyl; CO—O-aryl substituted with alkyl, alkoxy, halogen, CN, $CF_3$; CO—O-alkylenearyl unsubstituted or substituted with alkyl, alkoxy, halogen, CN, $CF_3$; CO—O-heteroaryl; CO—NH-aryl substituted with alkyl, alkoxy, halogen, CN, $CF_3$; CO—NH-alkylenearyl unsubstituted or substituted with alkyl, alkoxy, halogen, CN, $CF_3$; CO—NH-heteroaryl; $SO_2$—$NH_2$; or R1 and R2 together form a 5 or 6-membered ring which may optionally contain from 1 to 2 heteroatoms independently selected from the group consisting of nitrogen, oxygen and sulfur; and which may optionally bear 1 or 2 double bonds; and which may also be substituted by alkyl, halogenalkyl, aryl unsubstituted or substituted with alkyl, alkoxy, hydroxy, halogen, CN, $CF_3$, and/or heteroaryl; and which may also contain a carbonyl group; and which may also be condensed with aryl;

R3 and R4 are independently selected from the group consisting of H and cycloalkyl; or R3 and R4 together form a 5 or 6-membered ring which may optionally contain from 1 to 2 heteroatoms independently selected from the group consisting of nitrogen and oxygen atoms and which may also be substituted by aryl.

3. A compound according to claim 1, wherein:

R1 is selected from the group consisting of H, alkyl; cycloalkyl; alkylenealkoxy; alkylenecycloalkyl; aryl; alkylenearyl; heteroaryl; alkyleneheteroaryl substituted with halogen;

R2 is selected from the group consisting of alkylenealkoxy; alkylenecycloalkyl; CO-alkyl; CO-cycloalkyl; CO-alkylenearyl; CO-heteroaryl; CO—NH-alkylenearyl; CO—NH-aryl substituted with alkyl, alkoxy, halogen, CN, $CF_3$; CO—NH-alkylenearyl substituted with alkyl, alkoxy, halogen, CN, $CF_3$; CO—NH-heteroaryl; $SO_2$—$NH_2$; or R1 and R2 together form a 5 or 6-membered ring which may optionally contain from 1 to 2 heteroatoms independently selected from the group consisting of nitrogen, oxygen and sulfur; and which may optionally bear 1 or 2 double bonds; and which may also be substituted by alkyl, halogenalkyl, aryl unsubstituted or substituted with alkyl, alkoxy, hydroxy, halogen, CN, $CF_3$, and/or heteroaryl; and which may also contain a carbonyl group; and which may also be condensed with aryl;

R3 and R4 are independently selected from the group consisting of H and cycloalkyl; or R3 and R4 together form a ring selected from the group consisting of pyrrolidinyl, piperidinyl-p-phenyl, piperazinyl-p-phenyl and morpholino.

4. A compound according to claim 1, wherein R1 is only H if R2 does not contain a CO group.

5. A compound according to claim 1, wherein R3 and R4 are both H.

6. A pharmaceutical composition comprising:

(a) a compound corresponding to Formula I,

I

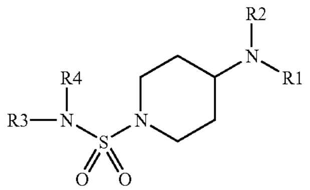

wherein

R1 is selected from the group consisting of H; alkyl; cycloalkyl; alkylenealkoxy; alkylenecycloalkyl; aryl unsubstituted or substituted by one or more alkyl, alkoxy, halogen, $CF_3$, CN; alkylenearyl; alkylenearylenealkyl; alkylenearylenehalogen; alkylenearyleneoxyalkyl, alkylenearylenedialkylamin; heteroaryl; alkyleneheteroaryl unsubstituted or substituted with alkyl, alkoxy, halogen, CN, $CF_3$;

R2 is selected from the group consisting of cycloalkyl; aryl unsubstituted or substituted with alkyl, alkoxy, halogen, CN, $CF_3$; alkylenearyl, unsubstituted or substituted, but not substituted by furan or furanyl; alkylenealkoxy; alkylenecycloalkyl; CO-alkyl; CO-cycloalkyl; CO-aryl substituted by alkyl, alkoxy, halogen, $CF_3$, CN; CO-alkylenearyl unsubstituted or substituted with alkyl, alkoxy, halogen, $CF_3$, CN; CO-heteroaryl unsubstituted or substituted by alkyl, alkoxy, halogen, $CF_3$, CN; CO—O-alkyl; CO—O-cycloalkyl; CO—O-aryl substituted with alkyl, alkoxy, halogen, CN, $CF_3$; CO—O-alkylenearyl unsubstituted or substituted with alkyl, alkoxy, halogen, CN, $CF_3$; CO—O-heteroaryl; CO—NH-alkyl; CO—NH-cycloalkyl; CO—NH-aryl substituted with alkyl, alkoxy, halogen, CN, $CF_3$; CO—NH-alkylenearyl unsubstituted or substituted with alkyl, alkoxy, halogen, CN, $CF_3$; CO—NH-heteroaryl; $SO_2$—$NH_2$; $SO_2$-alkyl; $SO_2$-aryl unsubstiuted or substituted by alkyl, alkoxy, halogen, $CF_3$, CN; or R1 and R2 together form a 5 or 6-membered ring which may optionally contain from 1 to 2 additional heteroatoms independently selected from the group consisting of nitrogen, oxygen and sulfur; and which may optionally bear 1 or 2 double bonds; and which may also be substituted by alkyl, halogenalkyl, aryl unsubstituted or substituted with alkyl, alkoxy, hydroxy, halogen, CN, $CF_3$, and/or heteroaryl; and which may also contain a carbonyl group; and which may also be condensed with aryl;

R3 and R4 are independently selected from the group consisting of H, cycloalkyl, cycloalkyl containing 1 or more heteroatoms selected from nitrogen and oxygen; cycloalkyl containing 1 or more heteroatoms selected from nitrogen and oxygen, and substituted with alkyl, alkoxy, halogen, $CF_3$, CN; aryl; aryl substituted with alkyl, alkoxy, halogen, $CF_3$, CN; heteroaryl; and heteroaryl substituted with alkyl, alkoxy, halogen, $CF_3$, CN; or R3 and R4 together form a 5 or 6-membered ring which may optionally contain from 1 to 2 heteroatoms independently selected from the group consisting of nitrogen and oxygen atoms and which may also be substituted by aryl or aryl substituted with alkyl, alkoxy, halogen, $CF_3$ and CN; their physiologically acceptable acid addition salts; and (b) at least one pharmaceutically acceptable auxiliary or carrier.

7. A pharmaceutical composition according to claim 6, wherein:

R1 is selected from the group consisting of H; alkyl; cycloalkyl; alkylenealkoxy; alkylenecycloalkyl; aryl; alkylenearyl; heteroaryl; alkyleneheteroaryl unsubstituted or substituted with halogen;

R2 is selected from the group consisting of cycloalkyl; aryl substituted with alkyl, alkoxy, halogen, CN, $CF_3$; alkylenearyl, unsubstituted or substituted, but not substituted by furan or furanyl; alkylenealkoxy; alkylenecycloalkyl; CO-alkyl; CO-cycloalkyl; CO-alkylenearyl; CO-heteroaryl; CO—O-alkyl; CO—O-cycloalkyl; CO—O-aryl substituted with alkyl, alkoxy, halogen, CN, $CF_3$; CO—O-alkylenearyl unsubstituted or substituted with alkyl, alkoxy, halogen, CN, $CF_3$; CO—O-heteroaryl; CO—NH-aryl substituted with alkyl, alkoxy, halogen, CN, $CF_3$; CO—NH-alkylenearyl unsubstituted or substituted with alkyl, alkoxy, halogen, CN, $CF_3$; CO—NH-heteroaryl; $SO_2$—$NH_2$; or R1 and R2 together form a 5 or 6-membered ring which may optionally contain from 1 to 2 heteroatoms independently selected from the group consisting of nitrogen, oxygen and sulfur; and which may optionally bear 1 or 2 double bonds; and which may also be substituted by alkyl, halogenalkyl, aryl unsubstituted or substituted with alkyl, alkoxy, hydroxy, halogen, CN, $CF_3$, and/or heteroaryl; and which may also contain a carbonyl group; and which may also be condensed with aryl;

R3 and R4 are independently selected from the group consisting of H and cycloalkyl; or R3 and R4 together form a 5 or 6-membered ring which may optionally contain from 1 to 2 heteroatoms independently selected from the group consisting of nitrogen and oxygen atoms and which may also be substituted by aryl.

8. A pharmaceutical composition according to claim 6, wherein:

R1 is selected from the group consisting of alkyl; cycloalkyl; alkylenealkoxy; alkylenecycloalkyl; aryl; alkylenearyl; heteroaryl; alkyleneheteroaryl substituted with halogen;

R2 is selected from the group consisting of alkylenealkoxy; alkylenecycloalkyl; CO-alkyl; CO-cycloalkyl; CO-alkylenearyl; CO-heteroaryl; CO—NH-alkylenearyl; CO—NH-aryl substituted with alkyl, alkoxy, halogen, CN, $CF_3$; CO—NH-alkylenearyl substituted with alkyl, alkoxy, halogen, CN, $CF_3$; CO—NH-heteroaryl; $SO_2$—$NH_2$; or R1 and R2 together form a 5 or 6-membered ring which may optionally contain from 1 to 2 heteroatoms independently selected from the group consisting of nitrogen, oxygen and sulfur; and which may optionally bear 1 or 2 double bonds; and which may also be substituted by alkyl, halogenalkyl, aryl unsubstituted or substituted with alkyl, alkoxy, hydroxy, halogen, CN, $CF_3$, and/or heteroaryl; and which may also contain a carbonyl group; and which may also be condensed with aryl;

R3 and R4 are independently selected from the group consisting of H and cycloalkyl; or R3 and R4 together form a ring selected from the group consisting of pyrrolidinyl, piperidinyl-p-phenyl, piperazinyl-p-phenyl and morpholino.

9. A pharmaceutical composition according to claim 6, wherein R1 is only H if R2 does not contain a CO group.

10. A pharmaceutical composition according to claim 6, wherein R3 and R4 are both H.

11. A process for preparing a compound corresponding to Formula I

I

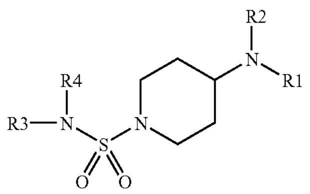

wherein

R1 is selected from the group consisting of H; alkyl; cycloalkyl; alkylenealkoxy; alkylenecycloalkyl; aryl unsubstituted or substituted by one or more alkyl, alkoxy, halogen, $CF_3$, CN; alkylenearyl; alkylenearylenealkyl; alkylenearylenehalogen; alkylenearyleneoxyalkyl, alkylenearylenedialkylamin; heteroaryl; alkyleneheteroaryl unsubstituted or substituted with alkyl, alkoxy, halogen, CN, $CF_3$;

R2 is selected from the group consisting of cycloalkyl; aryl unsubstituted or substituted with alkyl, alkoxy, halogen, CN, $CF_3$; alkylenearyl, unsubstituted or substituted, but not substituted by furan or furanyl; alkylenealkoxy; alkylenecycloalkyl; heteroaryl; CO-alkyl; CO-cycloalkyl; CO-aryl substituted by alkyl, alkoxy, halogen, $CF_3$, CN; CO-alkylenearyl unsubstituted or substituted with alkyl, alkoxy, halogen, $CF_3$, CN; CO-heteroaryl unsubstituted or substituted by alkyl, alkoxy, halogen, $CF_3$, CN; CO—O-alkyl; CO—O-cycloalkyl; CO—O-aryl substituted with alkyl, alkoxy, halogen, CN, $CF_3$; CO—O-alkylenearyl unsubstituted or substituted with alkyl, alkoxy, halogen, CN, $CF_3$; CO—O-heteroaryl; CO—NH-alkyl; CO—NH-cycloalkyl; CO—NH-aryl substituted with alkyl, alkoxy, halogen, CN, $CF_3$; CO—NH-alkylenearyl unsubstituted or substituted with alkyl, alkoxy, halogen, CN, $CF_3$; CO—NH-heteroaryl; $SO_2$—$NH_2$; $SO_2$-alkyl; $SO_2$-aryl unsubstiuted or substituted by alkyl, alkoxy, halogen, $CF_3$, CN; or R1 and R2 together form a 5 or 6-membered ring which may optionally contain from 1 to 2 additional heteroatoms independently selected from the group consisting of nitrogen, oxygen and sulfur; and which may optionally bear 1 or 2 double bonds; and which may also be substituted by alkyl, halogenalkyl, aryl unsubstituted or substituted with alkyl, alkoxy, hydroxy, halogen, CN, $CF_3$, and/or heteroaryl; and which may also contain a carbonyl group; and which may also be condensed with aryl;

R3 and R4 are independently selected from the group consisting of H, cycloalkyl, cycloalkyl containing 1 or more heteroatoms selected from nitrogen and oxygen; cycloalkyl containing 1 or more heteroatoms selected from nitrogen and oxygen, and substituted with alkyl, alkoxy, halogen, $CF_3$, CN; aryl; aryl substituted with alkyl, alkoxy, halogen, $CF_3$, CN; heteroaryl; and heteroaryl substituted with alkyl, alkoxy, halogen, $CF_3$, CN; or R3 and R4 together form a 5 or 6-membered ring which may optionally contain from 1 to 2 heteroatoms independently selected from the group consisting of nitrogen and oxygen atoms and which may also be substituted by aryl or aryl substituted with alkyl, alkoxy, halogen, $CF_3$ and CN;

or a physiologically acceptable acid addition salt thereof, said process comprising:

(a) if R3 and R4 are both other than H, reacting a compound of Formula II

II

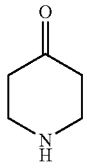

with a sulfamoylchloride of Formula III

III

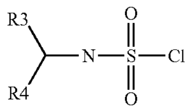

to give a compound of Formula IV

IV

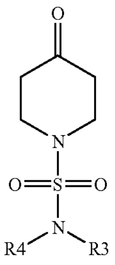

reacting the compound of Formula IV with an amine of formula $H_2NR1$ to give a compound of Formula V

V

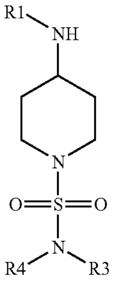

and further reacting the compound of Formula V with R2X, wherein X is selected from the group consisting of Cl, Br, and I, to give a compound of Formula I

I

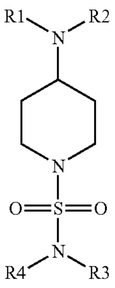

or (b) if R3 and R4 are both other than H, reacting a compound of Formula IV with an amine of formula HNR1R2 to give a compound of Formula I

I

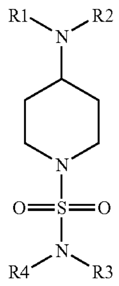

or (c) if R3 and R4 are both H, reacting a compound of Formula II

II

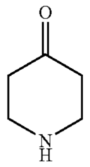

with a sulfamoylchloride having a protective group, or with a tert.butyloxycarbonyl compound of Formula VIa, or with a compound of Formula VIb, wherein PG represents a protecting group VIa

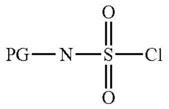

VIb

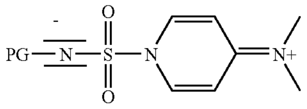

to give a compound of formula VII

VII

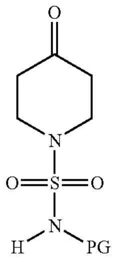

and then reacting the compound of Formula VII with an amine of formula H2NR1 to give a compound of Formula VIII

VIII

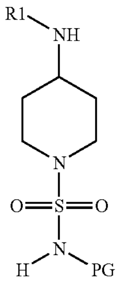

and further reacting the compound of Formula VIII with R2X, wherein X is selected from the group consisting of Cl, Br, and I, to give a compound of Formula IX

IX

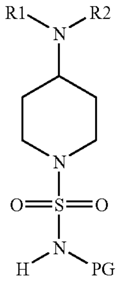

and subsequently cleaving off the protecting group PG from the compound of Formula IX to yield a compound of Formula I wherein R3 and R4 are both H; or (d) if R3 and R4 are both H, reacting a compound of Formula VII with an amine of the formula HNR1R2 to give a compound of Formula IX

IX

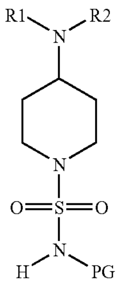

and subsequently cleaving off the protecting group PG from the compound of formula IX to yield a compound of Formula I wherein R3 and R4 are both H; or (e) if R2 contains a methylene spacer $CH_2$, reacting a compound of Formula X

X

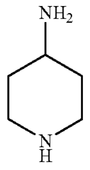

with a protecting agent PG, to give a compound of formula XI

XI

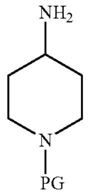

and then reacting the compound of Formula XI with an aldehyde of formula R2'- CHO, wherein R2' is selected from the group consisting of alkyl; cycloalkyl; alkylenearyl, unsubstituted or substituted, but not substituted by furan or furanyl; alkylenealkoxy; and alkylenecycloalkyl, to give a compound of Formula XII

XII

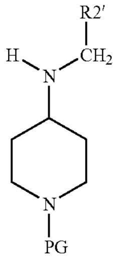

and then cleaving off the protecting group PG from the compound of Formula XII and reacting the resulting unprotected compound with a sulfamoylchloride of Formula $ClSO_2—NH_2$ to give a compound of Formula I; or (f) if R2 contains a methylene spacer $CH_2$, cleaving off the protecting group PG from a compound of Formula XII and then reacting the resulting unprotected compound with sulfamoylchloride, or with a tert.butyloxycarbonyl compound of Formula VIa, or with a compound of Formula VIb, wherein PG represents a protecting group VIa

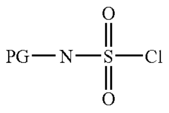

-continued

VIb

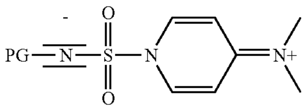

to give a compound of Formula XIII

XIII

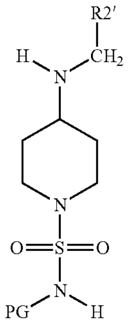

and subsequently cleaving off the protecting group PG from the obtained intermediate product, to give a compound of Formula I wherein R3 and R4 are both H;

(g) if R2 contains a methylene spacer $CH_2$, reacting a compound of Formula X

X

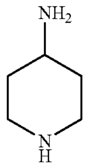

with a protecting agent PG, to give a compound of formula XI

XI

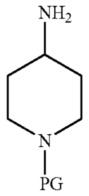

and then reacting the compound of Formula XI with a ketone of Formula R2'-COR 1', wherein R1' is selected from the group consisting of alkyl; alkylenealkoxy; alkylenecycloalkyl; alkylenearyl; alkylenearylenealkyl; alkylenearylenehalogen; alkylenearyleneoxyalkyl, alkylenearylenedialkylamin; and alkyleneheteroaryl unsubstituted or substituted with alkyl, alkoxy, halogen, CN or $CF_3$ and R2' is selected from the group consisting of alkyl; cycloalkyl; alkylenearyl, unsubstituted or substituted, but not substituted by furan or furanyl; alkylenealkoxy; and alkylenecycloalkyl;

to give a compound of Formula XIV,

XIV

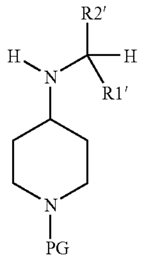

and then cleaving off the protecting group PG of compound of Formula XIV and reacting the unprotected compound with a sulfamoylchloride, or with a tert.butyloxycarbonyl compound of Formula VIa, or with a compound of Formula VIb, wherein PG represents a protecting group, VIa

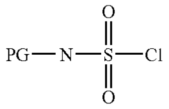

VIb

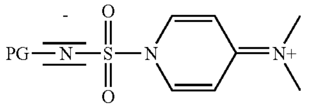

to give a compound of Formula XV

XV

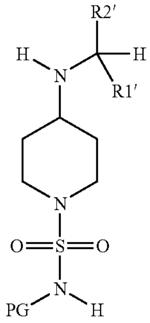

and then cleaving off the protecting group PG from the compound of Formula XV, to yield a compound of Formula I wherein R3 and R4 are both H, (h) reacting a compound of Formula II

II

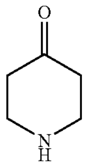

with a protecting agent PG to give a compound of Formula XVII

XVII

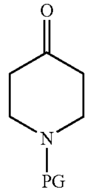

reacting the compound of Formula XVII with an amine of Formula NHR1R2 to give a compound of Formula XVIII,

XVIII

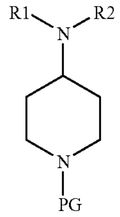

cleaving off the protecting group PG of the compound of Formula XVIII and reacting the unprotected compound with sulfamid to give a compound of Formula I, or reacting the unprotected compound with a compound of formula III to give a compound of Formula I, or reacting the unprotected compound with a compound of Formula VIa or Formula VIb to give a compound of Formula XIX

XIX

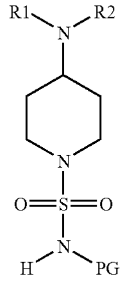

cleaving off the protecting group PG from the obtained intermediate product, to give a compound of Formula I;

(i) reacting a compound of Formula XVIIIa wherein R1 is H

XVIIIa

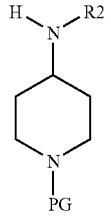

with a compound of Formula XX

R5-N=C=O XX wherein R5 is selected from the group consisting of alkyl; cycloalkyl; aryl substituted with alkyl, alkoxy, halogen, CN, $CF_3$; alkylenearyl unsubstituted or substituted with alkyl, alkoxy, halogen, CN or $CF_3$; and heteroaryl; to give a compound of Formula XXI

XXI

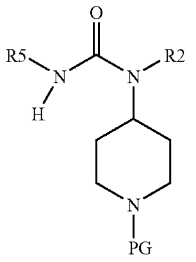

cleaving off the the protecting group PG of the compound of Formula XXI and reacting the unprotected compound with sulfamid to give a compound of Formula I, or reacting the unprotected compound with a compound of formula III to give a compound of Formula I, or reacting the unprotected compound with a compound of Formula VIa or Formula VIb to give a compound of Formula XXII

XXII

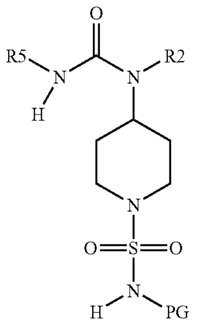

cleaving off the protecting group PG from the obtained intermediate product, to give a compound of Formula I;

(j) reacting a compound of Formula XVIIIa wherein R1 is H

XVIII

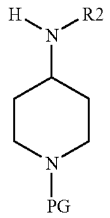

with a compound of formula XXIII

XXIII

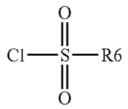

wherein R6 is selected from the group consisting of alkyl; aryl unsubstiuted or substituted by alkyl, alkoxy, halogen, $CF_3$ or CN;

to give a compound of Formula XXIV

XXIV

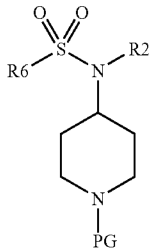

cleaving off the protecting group PG of the compound of Formula XXIV and reacting the unprotected compound is then reacted with sulfamid to give a compound of Formula I, or reacting the unprotected compound with a compound of Formula III to give a compound of Formula I, or reacting the unprotected compound with a compound of Formula VIa or Formula VIb to give a compound of Formula XXV

XXV

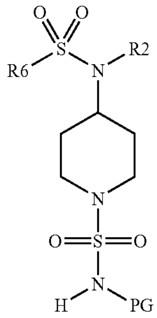

and cleaving off the protecting group PG from the obtained intermediate product, to give a compounds of Formula I, (k) reacting a compound of Formula XI

XI

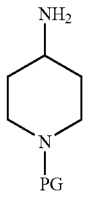

with a compound of Formula XXIII to give a compound of Formula XXVI

XXVI

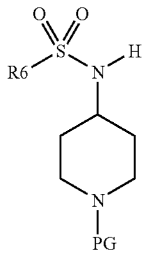

cleaving off the protecting group PG of the compound of Formula XXVI and reacting the unprotected compound with sulfamid to give a compound of Formula I, or reacting the unprotected compound with a compound of Formula III to give a compound of Formula I, or reacting the unprotected compound with a compound of Formula VIa or Formula VIb to give a compound of Formula XXVII

XXVII

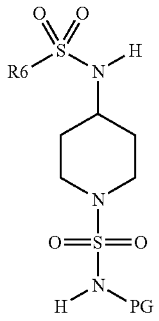

and cleaving off the protecting group PG from the obtained intermediate product, to give a compound of Formula I, (l) reacting a compound of Formula VIII

VIII

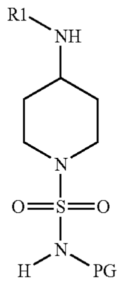

with a compound of Formula XX

R5-N═C═O XX to give a compound of Formula XXVIII

XXVIII

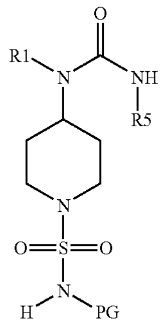

cleaving off the protecting group PG of the compound of Formula XXVIII to give a compound of Formula I (m) reacting a compound of Formula XI

XI

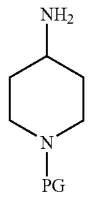

with a compound of formula XXIX

XXIX

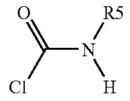

to give a compound of Formula XXX

XXX

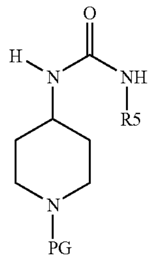

cleaving off the protecting group PG of the compound of Formula XXX to give a compound of Formula XXXI

XXXI

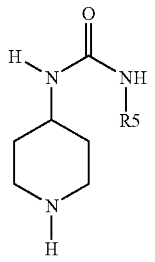

and wherein the compound of Formula XXXI is then reacted with sulfamoylchlorid of Formula III to give compounds of Formula I, or with a compound of Formulae VIa or VIb to give a compound of Formula XXXII

XXXII

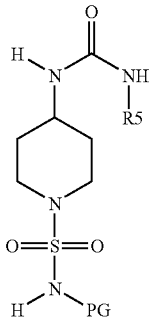

and then cleaving off the protecting group PG from the compound of Formula XXXII to give a compound of Formula I; and optionally converting a free base of Formula I into a corresponding physiologically acceptable acid addition salt, or converting an acid addition salt of a compound of Formula I into a corresponding free base of Formula I.

12. A process according to claim 11, wherein PG represents a tert.-butyloxycarbonyl protecting group.

13. A process according to claim 11 wherein:

R1 is selected from the group consisting of H; alkyl; cycloalkyl; alkylenealkoxy; alkylenecycloalkyl; aryl; alkylenearyl; heteroaryl; alkyleneheteroaryl unsubstituted or substituted with halogen;

R2 is selected from the group consisting of cycloalkyl; aryl substituted with alkyl, alkoxy, halogen, CN, $CF_3$; alkylenearyl, unsubstituted or substituted, but not substituted by furan or furanyl; alkylenealkoxy; alkylenecycloalkyl; CO-alkyl; CO-cycloalkyl; CO-alkylenearyl; CO-heteroaryl; CO—O-alkyl; CO—O-cycloalkyl; CO—O-aryl substituted with alkyl, alkoxy, halogen, CN, $CF_3$; CO—O-alkylenearyl unsubstituted or substituted with alkyl, alkoxy, halogen, CN, $CF_3$; CO—O-heteroaryl; CO—NH-aryl substituted with alkyl, alkoxy, halogen, CN, $CF_3$; CO—NH-alkylenearyl unsubstituted or substituted with alkyl, alkoxy, halogen, CN, $CF_3$; CO—NH-heteroaryl; $SO_2$—$NH_2$; or R1 and R2 together form a 5 or 6-membered ring which may optionally contain from 1 to 2 heteroatoms independently selected from the group consisting of nitrogen, oxygen and sulfur; and which may optionally bear 1 or 2 double bonds; and which may also be substituted by alkyl, halogenalkyl, aryl unsubstituted or substituted with at least one of alkyl, alkoxy, hydroxy, halogen, CN, $CF_3$, and heteroaryl; and which may also contain a carbonyl group; and which may also be condensed with aryl;

R3 and R4 are independently selected from the group consisting of H and cycloalkyl; or R3 and R4 together form a 5 or 6-membered ring which may optionally contain from 1 to 2 heteroatoms independently selected from the group consisting of nitrogen and oxygen atoms and which may also be substituted by aryl.

14. A process according to claim 11, wherein:

R1 is selected from the group consisting of alkyl; cycloalkyl; alkylenealkoxy; alkylenecycloalkyl; aryl; alkylenearyl; heteroaryl; alkyleneheteroaryl substituted with halogen;

R2 is selected from the group consisting of alkylenealkoxy; alkylenecycloalkyl; CO-alkyl; CO-cycloalkyl; CO-alkylenearyl; CO-heteroaryl; CO—NH-alkylenearyl; CO—NH-aryl substituted with alkyl, alkoxy, halogen, CN, $CF_3$; CO—NH-alkylenearyl substituted with alkyl, alkoxy, halogen, CN, $CF_3$; CO—NH-heteroaryl; $SO_2$—$NH_2$; or R1 and R2 together form a 5 or 6-membered ring which may optionally contain from 1 to 2 heteroatoms independently selected from the group consisting of nitrogen, oxygen and sulfur; and which may optionally bear 1 or 2 double bonds; and which may also be substituted by alkyl, halogenalkyl, aryl unsubstituted or substituted with at least one of alkyl, alkoxy, hydroxy, halogen, CN, $CF_3$, and heteroaryl; and which may also contain a carbonyl group; and which may also be condensed with aryl;

R3 and R4 are independently selected from the group consisting of H and cycloalkyl; or R3 and R4 together form a ring selected from the group consisting of pyrrolidinyl, piperidinyl-p-phenyl, piperazinyl-p-phenyl and morpholino.

15. A process according to claim 11, wherein R1 is only H if R2 does not contain a CO group.

16. A process according to claim 11, wherein R3 and R4 are both H.

17. A method of treating or inhibiting a disease or disorder selected from the group consisting of glaucoma, epilepsy, bipolar disorders, migraine, neuropathic pain, obesity, type II diabetes, and alcohol dependence, in a patient in need thereof, said method comprising administering to said patient a therapeutically effective amount of a compound corresponding to Formula I

I

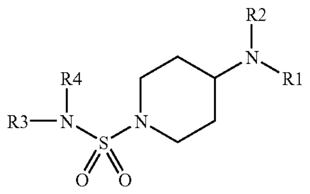

wherein

R1 is selected from the group consisting of H; alkyl; cycloalkyl; alkylenealkoxy; alkylenecycloalkyl; aryl unsubstituted or substituted by one or more alkyl, alkoxy, halogen, $CF_3$, CN; alkylenearyl; alkylenearylenealkyl; alkylenearylenehalogen; alkylenearyleneoxyalkyl, alkylenearylenedialkylamin; heteroaryl; alkyleneheteroaryl unsubstituted or substituted with alkyl, alkoxy, halogen, CN, $CF_3$;

R2 is selected from the group consisting of cycloalkyl; aryl unsubstituted or substituted with alkyl, alkoxy, halogen, CN, $CF_3$; alkylenearyl, unsubstituted or substituted, but not substituted by furan or furanyl; alkylenealkoxy; alkylenecycloalkyl; CO-alkyl; CO-cycloalkyl; CO-aryl substituted by alkyl, alkoxy, halogen, $CF_3$, CN; CO-alkylenearyl unsubstituted or substituted with alkyl, alkoxy, halogen, $CF_3$, CN; CO-heteroaryl unsubstituted or substituted by alkyl, alkoxy, halogen, $CF_3$, CN; CO—O-alkyl; CO—O-cycloalkyl; CO—O-aryl substituted with alkyl, alkoxy, halogen, CN, $CF_3$; CO—O-alkylenearyl unsubstituted or substituted with alkyl, alkoxy, halogen, CN, $CF_3$; CO—O-heteroaryl; CO—NH-alkyl; CO—NH-cycloalkyl; CO—NH-aryl substituted with alkyl, alkoxy, halogen, CN, $CF_3$; CO—NH-alkylenearyl unsubstituted or substituted with alkyl, alkoxy, halogen, CN, $CF_3$; CO—NH-heteroaryl; $SO_2$—$NH_2$; $SO_2$-alkyl; $SO_2$-aryl unsubstiuted or substituted by alkyl, alkoxy, halogen, $CF_3$, CN; or R1 and R2 together form a 5 or 6-membered ring which may optionally contain from 1 to 2 additional heteroatoms independently selected from the group consisting of nitrogen, oxygen and sulfur; and which may optionally bear 1 or 2 double bonds; and which may also be substituted by alkyl, halogenalkyl, aryl unsubstituted or substituted with at least one of alkyl, alkoxy, hydroxy, halogen, CN, $CF_3$, and heteroaryl; and which may also contain a carbonyl group; and which may also be condensed with aryl;

R3 and R4 are independently selected from the group consisting of H, cycloalkyl, cycloalkyl containing 1 or more heteroatoms selected from the group consisting of nitrogen and oxygen; cycloalkyl containing 1 or more heteroatoms selected from the group consisting of nitrogen and oxygen, and substituted with alkyl, alkoxy, halogen, $CF_3$, CN; aryl; aryl substituted with alkyl, alkoxy, halogen, $CF_3$, CN; heteroaryl; and heteroaryl substituted with alkyl, alkoxy, halogen, $CF_3$, CN; or R3 and R4 together form a 5 or 6-membered ring which may optionally contain from 1 to 2 heteroatoms independently selected from the group consisting of nitrogen and oxygen atoms and which may also be substituted by aryl or aryl substituted with alkyl, alkoxy, halogen, $CF_3$ and CN;

or a physiologically acceptable acid addition salt thereof.

18. A method according to claim 17, wherein said patient is a human.

* * * * *